US007956328B2

(12) United States Patent
Sundaram et al.

(10) Patent No.: US 7,956,328 B2
(45) Date of Patent: Jun. 7, 2011

(54) SYSTEM, DEVICE, AND METHODS FOR REAL-TIME SCREENING OF LIVE CELLS, BIOMARKERS, AND CHEMICAL SIGNATURES

(75) Inventors: S. Kamakshi Sundaram, Richland, WA (US); Brian J. Riley, West Richland, WA (US); Thomas J. Weber, Richland, WA (US); Colette A. Sacksteder, West Richland, WA (US); R. Shane Addleman, Benton City, WA (US)

(73) Assignee: Battelle Memorial Institute, Richland, WA (US)

( * ) Notice: Subject to any disclaimer, the term of this patent is extended or adjusted under 35 U.S.C. 154(b) by 111 days.

(21) Appl. No.: 12/511,833

(22) Filed: Jul. 29, 2009

(65) Prior Publication Data
US 2011/0024630 A1 Feb. 3, 2011

(51) Int. Cl.
*G01J 5/02* (2006.01)
(52) U.S. Cl. .................................. 250/339.11
(58) Field of Classification Search ............... 250/338.1, 250/339.08, 339.11
See application file for complete search history.

(56) References Cited

U.S. PATENT DOCUMENTS

2002/0155541 A1* 10/2002 Naughton et al. ........... 435/69.1
2004/0201848 A1 10/2004 Codner et al.

FOREIGN PATENT DOCUMENTS

| JP | 2008191054 | | 8/2008 |
| WO | 2009058853 | A2 | 5/2009 |
| WO | 2009081406 | A2 | 7/2009 |

OTHER PUBLICATIONS

Communication Relating to the Results of the Partial International Search.
Miyamoto, K., et al., In situ observation of a cell adhesion and megabolism using surface infrared spectroscopy, Cytotechnology, Kluwer Academic Publishers, DO, DOI 10.1007/S10616-007-9111-2, vol. 55, No. 2-3, Nov. 27, 2007, pp. 143-149.
Hutson, T. B., et al, A Technique for Monitoring Mammalian Cell Growth and Inhibition in Situ via Fourier Transform Infrared Spectroscopy, Analytical Biochemistry, Academic Press, Inc., New York, DOI 10.1016/003-2697(88)90040-1, vol. 174, No. 2, Nov. 1, 1988, pp. 415-422.
Shankaran, D. R., et al., Recent advancements in surface plasmon resonance immunosensors for detection of small molecules of biomedical, food and environmental interest, Sensors and Actuators B, Elsevier Sequoia S.A., Lausanne, DOI: 10.1016/J.SNB.2006.09.014, vol. 121, No. 1, Jan. 23, 2007, pp. 158-177.

(Continued)

*Primary Examiner* — David P Porta
*Assistant Examiner* — Mark R Gaworecki
(74) *Attorney, Agent, or Firm* — James D. Matheson

(57) ABSTRACT

An ATR-FTIR device and system are described that defect live-cell responses to stimuli and perturbations in real-time. The system and device can monitor perturbations resulting from exposures to various physical, chemical, and biological materials in real-time, as well as those sustained over a long period of time, including those associated with stimuli having unknown modes-of-action (e.g. nanoparticles). The device and system can also be used to identify specific chemical species or substances that profile cellular responses to these perturbations.

57 Claims, 16 Drawing Sheets

OTHER PUBLICATIONS

Ojeda, J. J., et al., In situ monitoring of the biofilm formation of *Pseudomonas putida* on hematite using flow-cell ATR-FTIR spectroscopy to investigate the formation of inner-sphere bonds between the bacteria and the mineral, Mineralogical Magazine, 2008 Mineralogical Society GB, vol. 72, No. 1, 2008, pp. 101-106.

Taylor, A. D., et al., Quantitative and simultaneous detection of four foodborne bacterial p;athogens with a multi-channel SPR sensor, Biosensors and Bioelectronics, Elsevier BV, DOI: 10.1016/J.BIOS. 2006.03.012, vol. 22, No. 5, Dec. 15, 2005, pp. 752-768.

Miyamoto, K., et al., In situ observation of a cell adhesion and megabolism using surface infrared spectroscopy, Cytotechnology, Kluwer Academic Publishers, DO, DOI 10.1007/S10616-007-9111-2, vol. 55, No. 2-3, Nov. 27, 2007, pp. 143-149.

Hutson, T. B., et al, A Technique for Monitoring Mammalian Cell Growth and Inhibition in Situ via Fourier Transform Infrared Spectroscopy, Analytical Biochemistry, Academic Press, Inc., New York, DOI 10.1016/003-2697(88)90040-1, vol. 174, No. 2, Nov. 1, 1988, pp. 415-422.

Shankaran, D. R., et al., Recent advancements in surface plasmon resonance immunosensors for detection of small molecules of biomedical, food and environmental interest, Sensors and Actuators B, Elsevier Sequoia S.A., Lausanne, DOI: 10.1016/J.SNB.2006.09.014, vol. 121, No. 1, Jan. 23, 2007, pp. 158-177.

Ojeda, J. J., et al., In situ monitoring of the biofilm formation of *Pseudomonas putida* on hematite using flow-cell ATR-FTIR spectroscopy to investigate the formation of inner-sphere bonds between the bacteria and the mineral, Mineralogical Magazine, 2008 Mineralogical Society GB, vol. 72, No. 1, 2008, pp. 101-106.

Taylor, A. D., et al., Quantitative and simultaneous detection of four foodborne bacterial p;athogens with a multi-channel SPR sensor, Biosensors and Bioelectronics, Elsevier BV, DOI: 10.1016/J.BIOS. 2006.03.012, vol. 22, No. 5, Dec. 15, 2005, pp. 752-768.

International Search Report/Written Opinion for International Application No. PCT/US2010/034940, International Filing Date May 14, 2010, Date of Mailing Jan. 7, 2011.

\* cited by examiner

SYSTEM, DEVICE, AND METHODS FOR REAL-TIME SCREENING OF LIVE CELLS, BIOMARKERS, AND CHEMICAL SIGNATURES

This invention was made with Government support under Contract DE-AC05-76RLO1830 awarded by the U.S. Department of Energy. The Government has certain rights in the invention.

FIELD OF THE INVENTION

The present invention relates generally to attenuated total reflectance (ATR) and Fourier transform infrared (FTIR) devices and methods for analysis of five cells and stimuli (e.g., physical, chemical, biological) that induce IR-observable changes in cells. More particularly, the invention relates to a combination ATR-FTIR device, system, and methods for in-situ screening of live cells and stimuli in real time.

BACKGROUND OF THE INVENTION

Biological applications of infrared (IR) spectroscopy have evolved substantially over the past several decades. Current efforts seek to understand information encoded by chemical bond changes that are observable in, and correlate with, higher order processes including, e.g. inflammation, proliferation, cell death, and cytostatic effects. The full potential of FTIR spectroscopy as a screening tool for toxicology related applications has not yet been fully realized due to several challenges. Principal among these challenges is keeping cells viable in the test cell while collecting IR spectra in situ. Attractive features of FTIR spectroscopy for system-level profiling include rapid, reagentless, non-destructive analysis of complex biological samples, thereby providing unbiased measurements of a biological system in near real-time. The non-destructive nature of FTIR can facilitate collection of detailed cell information as a function of time from a single experiment that defines dynamic chemical bond changes induced by selected stimuli (e.g., nanomatehals, chemical toxins, drugs, and etc.) In live cells. This objective view of system response may be particularly important when the mode of action for the respective stimulus is not known, as is frequently the case for nanomaterials and various chemical entities that overwhelm the capacity of conventional toxicological testing approaches to assess safety. While information encoded by IR-observable changes has yet to be fully understood and transcribed, this technology does have the potential to guide and improve application of global response assays for interrogating biological systems. One potential application is to define where in the IR regime qualitative or quantitative changes in FTIR-observable peaks occur to determine if an experimental system under investigation has been perturbed and then use this information to guide the application of global response assays in a cost-effective manner. This approach would allow interrogation of a biological system at selected times and frequencies that would reflect observable differences in the biological response. This is Important for stimuli whose modes-of-action are unknown and do not exert robust selective pressures on the system, such as cell death. While FTIR spectroscopy has sufficient sensitivity for automated and high throughput: screening, current ATR configurations do not allow for the maintenance and monitoring of live-cells within an ATR/FTIR device in order to utilize this spectroscopic sensitivity. Accordingly, new systems, devices, and processes are needed that provide for monitoring, screening, and measurement of live-cell responses to perturbations over extended periods of time, e.g., over 24 hours.

SUMMARY OF THE INVENTION

In one aspect, the invention is a device for monitoring live cells in real-time for extended periods of time, i.e., greater than 24 hours. The device includes live cells of at least one biological organism at a preselected confluence level affixed to a structured growth material attached to a surface of an ATR substrate within a growth-supporting environment. The ATR substrate in the growth supporting environment couples to, and interfaces with, an infrared instrument, e.g., an FTIR: instrument.

In various embodiments, the ATR substrate includes a material selected from zinc selenide (ZnSe); zinc sulfide (ZnS); silicon (Si); germanium (Ge) (crystalline); or amorphous materials transmitting IR (AMTIR). In various embodiments, AMTIR glasses include, but are not limited to, Ge—As—Se (AMTIR-1); As—Se (AMTIR-2); Ge—Sb—Se (AMTIR-2); As—Se (AMTIR-4); As—S (AMTIR-6); As—Se—Te; like chalcogenides; glasses transparent in infrared regions of interest including, e.g., heavy metal oxides that are transparent in the mid-IR; and combinations of these materials, in one embodiment, the ATR substrate is a 45° ZnSe, 12-bounce crystal, in various embodiments, the ATR substrate includes a beveled edge of an angle with respect to the top surface of the substrate selected in the range from 30° to 80°.

The growth-supporting environment is an enclosure vessel that includes at least one port for introduction or removal of cell nutrient (culture) media, fluids, gases, and/or other constituents. The growth-supporting environment further includes a trough with at least one side wall oriented at a preselected angle that minimizes splashing and maintains nutrient media or biological fluids in direct contact with live cells on the ATR substrate. The trough surrounds the ATR substrate to minimize agitation of the cell growth surface upon movement of the enclosure vessel. The angle of incline of the trough is preferably selected in the range from about 40° to 90°, but is not limited thereto. The surface of the ATR substrate can be coated with a chemical or functionalization layer that: 1) assists cell adhesion, 2) improves information content of IR spectra, and/or 3) improves signal-to-noise values. The chemically-modified surface also provides an interface upon which cells can function without a toxic or atypical response that may be induced by the ATR substrate. Surface, and functionalization, chemistries range from coatings that promote cell attachment (e.g., FIBRONECTIN®) to advanced chemical or biological surface functionalization methods that provide selected properties such as maintaining specialized cell functions or maximizing volumes of cells sampled spectroscopically by the ATR method. The growth-supporting environment further includes a viewport (e.g., on the lid of the enclosure vessel directly above the ATR substrate) that can be used to monitor condition (i.e., confluency and morphology) of live cells at the surface of the ATR substrate, e.g., in conjunction with transmission-mode optical microscopy or another imaging technology. The growth-supporting environment further includes a heater that provides temperature modulation and control within the enclosure environment. Temperatures for cell growth can be selected in the range from about room temperature (~25° C.) to body temperature (~37°C.), but temperatures are otherwise not limited. The growth-supporting environment can further include at least one sensor. Sensors include, but are not limited to, e.g., gas sensors, moisture sensors, humidity sensors, metabolite sensors, pH sensors, temperature sensors, and the like sensors, including combinations of these sensor types, in one embodiment, the sensor monitors concentration of at least one gas (e.g., $CO_2$) within the supporting environment.

In another embodiment, the growth-supporting environment includes a humidifier that provides a preselected humidify level within the supporting environment, e.g., in the range up to 100%. The growth-supporting environment further includes a lid component that provides viewing and imaging of internal contents of the growth-supporting environment or be customized to allow access to the internal chamber for addition of stimuli.

In one embodiment, a functional layer and interface are positioned between the transduction (optical) element (e.g., ATR substrate) and the sensing media (cells). Appropriately designed surface chemistry modifiers can be used to promote cell adhesion and functioning, to reduce effects of the optical media on normal cell functions, and to provide better sample-to-sample consistency. Surface modifiers can include protein coating such as FIBRONECTIN®, to chemical monolayers. Surface modifiers can be applied as a monolayer coating of molecules covalently or otherwise bound to the substrate. Monolayers provide minimal optical signature/attenuation while providing the ability to tailor the optical interface biochemically. Monolayer configurations ideally promote a reproducible surface that allows consistent cell binding sites and a high degree of reproducibility. The monolayer can also isolate and stabilize the optical surface from the nutrient medium ox other biological fluid thereby preventing degradation of the optical surface. Further, the monolayer can eliminate potential leaching of toxic materials (e.g., heavy metals such as, e.g., Pb, Se, Ge, As) out of the ATR substrate, which can promote cell death in the absence of any toxic marker.

In another aspect, the present invention includes a system that provides continuous monitoring of live-cells in real-time for extended time, i.e., greater than or equal to about 24 hours. The system includes a growth support environment that includes a containment vessel that defines an enclosure. The system also includes an ATR substrate suitably positioned within the growth-supporting environment that includes live cells that are affixed or attached to a structured material on the surface of the ATR substrate. A cell nutrient medium provides continuous nutrition to the cells maintained on the ATR substrate therein. The growth-supporting environment is detachably coupled to an infrared instrument (e.g., spectrometer) for screening and monitoring of the live cells in real-time. The ATR substrate aligns with the FTIR detector and instrument and can remain so aligned for the entire life-cycle of cells being monitored. Instrument alignment can be maintained using an alignment step inserted between data collection steps in order to correct for drift of instrument optics over the duration of the experiment, e.g., using a data collection macro.

In one embodiment, the structured growth material fixed and attached to the ATR substrate includes a cell growth reagent that provides continuous nutrition to live cells of at least one biological organism. The monitoring system can further include a temperature modulating/controlling device that maintains selected temperatures in the containment vessel of the growth-supporting environment. The monitoring system can further be configured with a humidity control device that maintains a selected humidify level within the enclosure vessel. At least one port is provided for introducing a preselected physiologic gas, a chemical or biological constituent, an atmospheric gas, and/or a preselected stimulus (e.g., physical, chemical, biological, and combinations of these types of stimuli). At least one port present in the enclosure or the containment vessel provides for introduction of any of a variety of preselected fluids including, e.g., gases, and liquids, as well as cell nutrients, and/or other reagents and removal of, e.g., metabolic wastes for analysis and data correlation. The growth-supporting environment when coupled to the FTIR instrument provides continuous near real-time data of live cells over a preselected time interval. In one embodiment, continuous near real-time, live-cell data in the FTIR instrument can be collected over a continuous time interval of $\geq 24$ hours. The system containment vessel can include a lid that provides containment of a cell nutrient fluid within the enclosure vessel. An infrared radiation source is operatively coupled to the ATR substrate that propagates the infrared radiation evanescently through the ATR substrate in at least one optical mode, e.g., ATR mode. A detector detects the absorptions from the evanescent wave transmitted through the ATR substrate that provides for real-time monitoring of live cells in contact with the ATR substrate.

The system can also include a $CO_2$ remediation system or device for monitoring and remediation of the amount of $CO_2$ present in the enclosure vessel, in various embodiments, various sensors and sensor components are incorporated to monitor different aspects of the system. Sensors include, but are not limited to, e.g., gas sensors, moisture sensors, humidify sensors, metabolite sensors, pH sensors, temperature sensors, and the like sensors, including combinations of these sensors. At least one port (e.g., on the lid of the enclosure vessel directly above the ATR substrate) can be used as a viewport that provides for monitoring the condition (i.e., confluency and morphology) of live cells at the surface of the ATR substrate using transmission-mode optical microscopy as well as other imaging technologies.

In one embodiment, the system includes at least two ATR substrates, a first substrate is for a reference sample; and at least a second substrate is for a sample for monitoring a preselected confluence layer or level of live cells from at least one biological organism. In another embodiment, the system includes at feast two ATR substrates mounted to a carousel stage. The carousel stage can be rotated (e.g., horizontally clockwise or counterclockwise, or vertically) and aligned to one or more optical detection systems or devices, e.g., about a center or other axis point that allows loading and continuous monitoring of multiple live cell samples simultaneously in real time for monitoring cell factors such as growth, viability, health, response, toxicity, and death on any of the samples loaded onto the carousel stage. The ATR substrates mounted in the carousel allow any of the live cell samples to be properly aligned and monitored as a function of time. In another embodiment, the carousel stage can include one or more reference samples for any of a preselected number of actual samples for independent analysis. The ATR substrates can include sides or edges that are at preselected angles with respect to the surface of the ATR substrate in the range from about 30° to 70°.

In various other embodiments, the system can be configured with a plurality of sample chambers or wells, e.g., a 6-well; a 96-well, or a greater numbers of wells. Each chamber or well includes a separate, built-in ATR substrate. Alternatively, multiple chambers can be integrated with advanced optics of a combinatorial chemistry/biological design for rapid combinatorial screening of live cells.

In one embodiment (basic design), the system includes more than one ATR chamber and substrate. Each substrate includes individual optics for directing an incoming IR beam from an IR source into the ATR substrate and directing an outgoing IR beam from the ATR substrate to a detector. In this system, multiple samples can be assembled and run simultaneously or sequentially.

In another embodiment (integrated design), the system includes more than one ATR chamber and substrate. Each ATR chamber and substrate is optically coupled to a single IR source and defector. In this system, multiple samples can be assembled and run simultaneously or sequentially. The system includes a moving mirror system that reflects the incoming IR beam from the IR source to each ATR chamber and substrate and another moving mirror system directs the outgoing IR beam from each ATR chamber and substrate to a single detector for analysis. The moving mirror systems can be operated to run multiple samples simultaneously or sequentially. Components of the integrated design can be miniaturized. For example: 1) the ATR substrate thickness can be varied to facilitate: a preselected number of bounces, a desired depth of penetration, and a desired analysis window; 2) optics for incoming and outgoing IR beams can be miniaturized at a component-level or at a planar-level; and 3) different IR propagation modes can be used including, e.g., a nanoscale surface plasmon for different length scales. In various other embodiments, automation of components of all equipment designs and levels are also envisioned.

In another aspect, the invention is a method for growing live cells that are fixed and attached to a surface of an ATR substrate at a preselected confluence or level thereon for continuous monitoring of the live cells. The method includes the steps: introducing a structured growth material as a thin film over the surface of the ATR substrate. The structured growth material includes a preselected quantity of defined material and a growth reagent therein; and seeding a preselected quantity of live cells of at least one biological organism to the thin film that is fixed and attached to the surface of the ATR substrate. The seeded live cells attach to, and maintain viability in contact with, the ATR substrate or the functionalization layer on the substrate. Presence of a nutrient medium places and maintains cells on the surface of the ATR substrate to enable sampling of the cell volume via the evanescent wave and IR spectroscopy. The ATR substrate Can be cleaned to remove surface coatings and can be further sterilized to permit recycling. The enclosure vessel and its components can be made of preselected materials that permit components, including the ATR substrate, to be autoclaved to sterilize the components.

In yet another aspect, the invention also includes a method for monitoring live cells in a biological process in real-time. The method includes the steps of: coupling a growth-supporting environment that includes an ATR substrate to an IR detector of an IR instrument that operably aligns an IR beam and IR optics in said instrument to said ATR substrate. The ATR substrate couples with an IR detector of an IR instrument. The step of coupling the ATR substrate to the FTIR instrument includes the step of aligning the ATR substrate using a peak-to-peak value in the centerburst of an interferogram in concert with alignment and detector gain settings of the instrument. The ATR substrate includes a confluent layer of live cells of at least one biological organism on a structured growth material that is fixed and attached to a surface of the ATR substrate. A preselected chemical or material can be introduced as a stimulus to the nutrient medium that is in contact with live cells in the confluent layer that is affixed to the ATR substrate. Response of the live cells to the introduced stimuli can then be continuously monitored and determined over a preselected time interval in real-time by probing the live cells with infrared energy in concert with at least one spectroscopic property. The preselected stimuli represent any physical, chemical, or biological materials, combinations of these stimuli that produce IR observable changes in the live cells of the system. The method can include the step of analyzing the response of live cells on the ATR substrate to a particokinetic property as a function of time. For example, a particle can be monitored using a characteristic absorption signature in the radiation range being analyzed. For example, $SiO_2$ nanoparticles have an absorption peak in the mid-IR range. In one embodiment, the particokinetic property being monitored is a particle settling rate. In another embodiment, the step of continuously monitoring includes monitoring at least one spectroscopic property. In one configuration, continuously monitoring includes analyzing a chemometric property as a function of time. The method further includes the step of ascertaining health of the live cells as a function of time. The step of ascertaining health of the live cells can include determining IR signatures associated with metabolites and chemicals as a function of time for assessment of the cell condition or health, in various embodiments, continuous monitoring of live cells includes continuously monitoring at least one spectroscopic properly, Spectroscopic properties include, but are not limited to, IR peaks (e.g., position, shape, and area) associated with, e.g., cell membrane lipids (e.g., symmetric and asymmetric stretching for $CH_2$ and $CH_3$). In one embodiment, continuous monitoring is performed over a preselected time interval that is $\geq 24$ hours. The step of continuously monitoring also includes screening the live cells continuously with an evanescent IR wave transmitted from an IR source as a function of time. The step of monitoring can further include the step of determining response of live cells to a potential toxin (e.g., a nanotoxin) or other biological perturbation introduced to the nutrient medium in real time by spectroscopically measuring an IR signature, e.g., of a nanotoxin as a function of time to ascertain the health condition of the cells.

In one embodiment according to the method of the invention, nanoparticles of silica that have a mid-IR observable absorption signature are used as a cell toxin (i.e., nanofoxin). Settling of the IR-absorbing particles is monitored as a function of time, while simultaneously monitoring cell growth and/or death. The method includes continuously monitoring increases in absorbances of mid-IR absorption peaks (e.g., 1116 $cm^{-1}$ for silica) and/or monitoring corresponding decreases in absorbances of cell membrane peaks as a function of time. Monitoring can include the step of determining a base-line shift in live-cell responses as determined from at least a first spectral plot against live-cell responses as determined from at least a second spectral plot, both as functions of time, in one embodiment, continuous monitoring includes comparing spectral differences in a $1^{st}$ plot at the start of an experiment and a $2^{nd}$ plot at the end of an experiment to assess changes in the condition of the live cells over a preselected interval of time. In another embodiment, continuous monitoring includes comparing spectral differences in at least an $(N+1)^{st}$ plot with at least an $N^{th}$ plot to assess changes in condition of said live cells over a preselected interval of time. Live cells can be probed on the ATR substrate in real-time with a preselected wavelength of electromagnetic radiation e.g., mid-IR (2.5 μm to 25 μm); far-IR (25 μm to 300 μm); and/or millimeter/THz wave regimes. In addition, this approach can also be used for tracking other physical/chemical, and/or biological changes including, e.g., radiation exposure that may take place prior to seeding cells onto the ATR substrate in the enclosure vessel. The health or condition of live-cells can be monitored as a function of time by determining IR signatures of metabolites and chemicals within the nutrient medium as well as IR signatures that represent changes in cellular chemistry/structure (particochemicokinetics) and biochemical (particochembiokinetics) processes as a function of time for analysis thereof. The method includes the step of determining a spectroscopic property of live cells in situ as a function of time and further includes analyzing and plotting a spectral representation of various spectroscopic properties for the cells being monitored as a function of time.

DETAILED DESCRIPTION

A new ATR system, device, and methods are disclosed that provide the ability to screen live cells and live-cell responses (i.e., live-cell spectroscopy) to system perturbations, including screening of potentially toxic conditions and materials in real-time, including, but not limited to. e.g., toxic nanomaterials. The ATR system and device include new materials, new sealing methods, greater capacity, means for controlling the temperature, and means for controlling $CO_2$ exposure and humidity through external ports. While a preferred embodiment of the present invention will now be described, the invention is not limited thereto. From the description, it will be apparent that various modifications, alterations and substitutions may also be made without departing from the spirit of the invention as set forth in the scope of the claims listed hereafter. Accordingly, the description of the preferred embodiment should be seen as illustrative only and not limiting.

Figure 1:
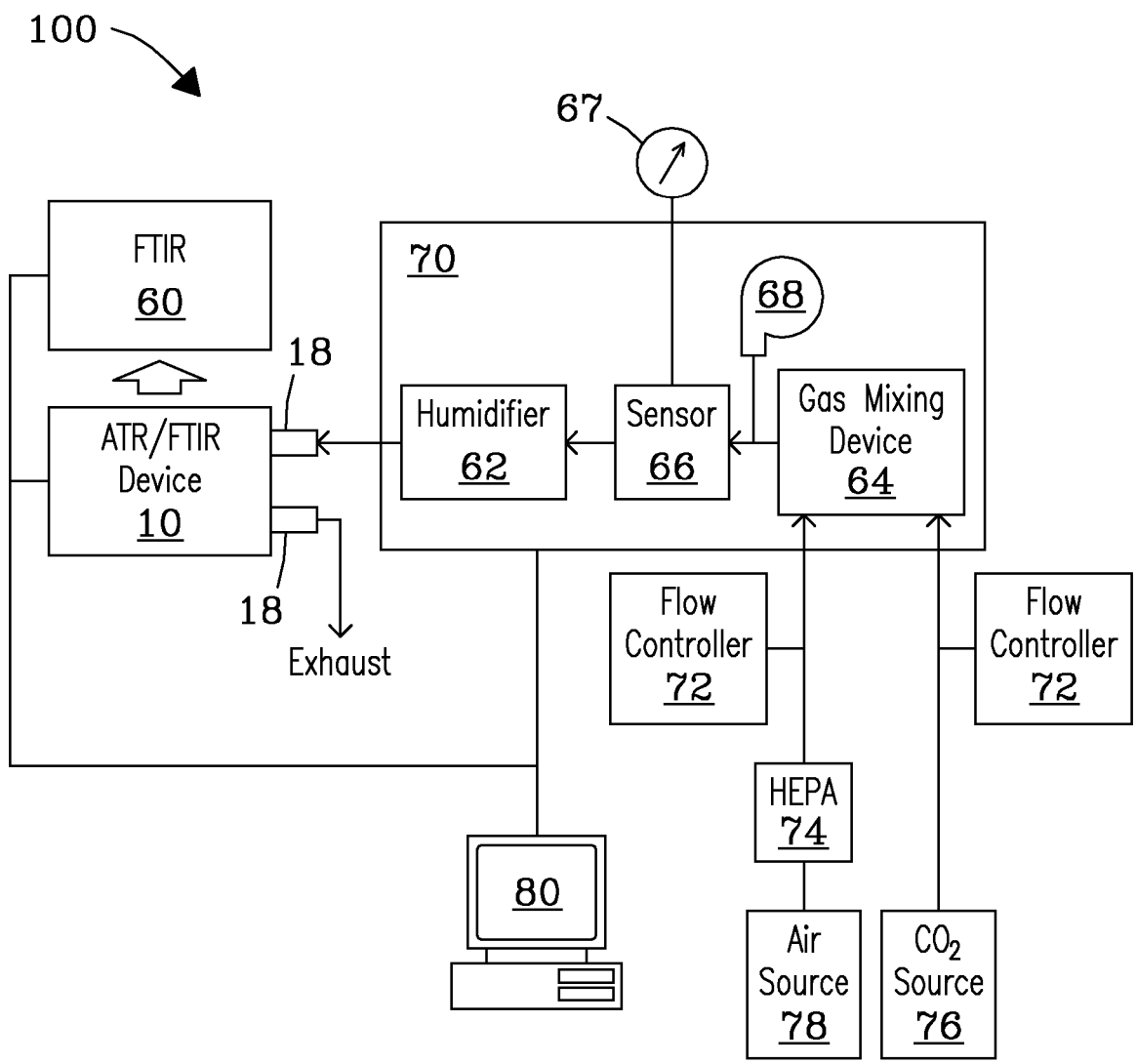
FIG. 1 shows an exemplary FTIR system that includes an ATR device (growth-supporting environment) of a self-inclusive enclosure design for real-time screening and monitoring of live cells, markers, and signatures, according to an embodiment of the invention.

FIG. 1 shows an exemplary FTIR system 100 for real-time screening and monitoring of live cells, biomarkers, and chemical signatures, according to an embodiment of the invention. System 100 is configured with an ATR device 10 (growth-supporting environment 10) of a self-inclusive enclosure design that provides environmental control and nutrient support for growth and maintenance of live cells. Growth-supporting environment 10 includes an ATR substrate (described in reference to FIG. 2b) that allows for real-time monitoring and analysis of live cells, as well as other analytes and constituents in conjunction with an FTIR instrument 60 to which it couples, which allows monitoring of responses in live cells grown within the device in real-time over an extended time period. Gas concentrations (e.g., $O_2$ and $CO_2$), humidity, and temperature control within growth-supporting environment 10 needed for proper cell growth are maintained and controlled, e.g., in conjunction with various devices including, but not limited to, e.g., input devices; transfer devices; flow control devices; regulation devices; measurement devices; heating devices; pumping devices; and other associated devices and components, input devices include, but are not limited to, e.g., gas sources; gas input devices; gas control devices; gas heating devices; fluid sources; fluid input devices; fluid control devices; heating devices; humidifiers; drug delivery devices; temperature control devices, and like devices, including combinations of these devices, in the figure, an input device 70 (Simplex Scientific, Middleton, Wis., USA) custom-built to control $CO_2$ and humidity is coupled to growth-supporting environment 10. Input device 70 includes a humidifier 62 that delivers moist air to the enclosure vessel in the range up to saturation to minimize fluid losses from evaporation; a gas mixing device 64 (e.g., a "T" tube) that mixes $CO_2$ and compressed air at a preselected ratio prior to delivery to enclosure vessel 10; a sensor 66 that measures, e.g., $CO_2$ concentration in the air delivered to enclosure vessel 10, e.g., in conjunction with a sensor display 67; and a pump 68 that delivers gases from respective gas sources to mixing device 64. In the figure, $CO_2$ source 76 (e.g., a $CO_2$ tank) and air source 78 (e.g., ambient air or compressed air) couple to input device 70 each delivering a respective gas to gas mixing device 64 in input device 70 for further processing, input device 70 can further include a heating device (not shown) to provide temperature control when needed, in the instant design, room air, if used, is cleaned of biological and other contaminants using, e.g., a filter 74 (e.g., HERA filter, fritted glass filters; or another suitable filter) that maintains the sterile environment within enclosure vessel 10. Quantity of gas introduced to input device 70 from each of $CO_2$ source 76 (e.g., a $CO_2$ tank) and air source 78 (e.g., ambient air or compressed air) can be regulated, e.g., in conjunction with a flow controller 72. In the figure, input device 70, ATR device 10, and FTIR instrument 60 can be individually or collectively interfaced to a computer 80 to provide: 1) environmental control including, but not limited to, e.g., gas flow device control; humidity control, temperature control; 2) FTIR instrument operation and control; and 3) data storage and data analysis. Sensor 66 can be configured to monitor gas concentrations delivered to enclosure vessel 10 and provide feedback to input device 70 to increase flow of one or more gas concentrations should they fall below a critical level to bring the gas concentration back to the desired level in the enclosure vessel. In an alternative configuration, a sensor 66 can be placed or incorporated within growth-supporting environment 10 to provide a direct measurement of gas concentrations within the enclosure vessel in real-time. In another alternate configuration, a sensor 66 can be used to measure concentration of an undesired gas, e.g., a respiration gas (e.g., $CO_2$). If the level of the respiration gas increases to an undesired level, sensor 66 can signal, e.g., input device 70 to increase the level of a desired gas (e.g., air or $O_2$). Concentration levels of both desired and undesired gases can thus be controlled, e.g., via a feedback loop mechanism. While a single input device has been shown and described, the invention is not limited thereto. All devices and components as will be selected by those of skill in the spectroscopic arts in view of the disclosure are within the scope of the invention.

Growth-Supporting Environment

Enclosure Vessel

Figure 2A:
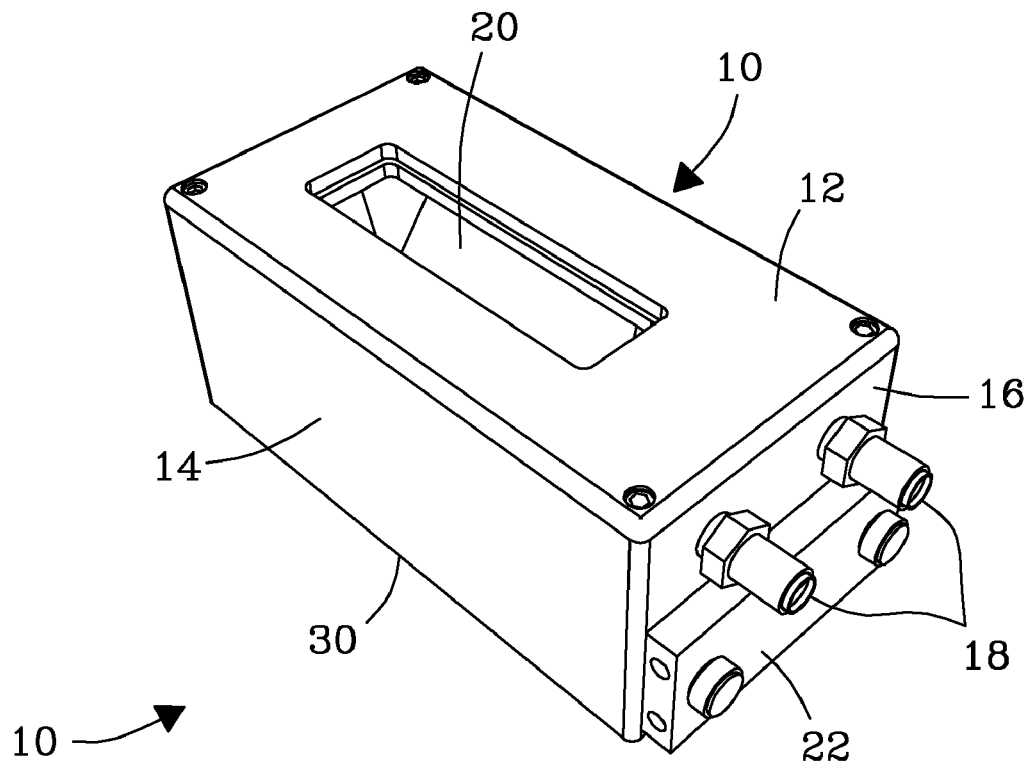
FIGS. 2a-2e show different views of the growth-supporting environment (enclosure vessel).

FIGS. 2a-2e present different views of the ATR-FTIR device 10 (growth-supporting environment 10) used for real-time spectroscopy of five cells, markers, and signatures, according to an embodiment of the invention. FIG. 2a shows a perspective view of ATR device 10. Growth-supporting environment 10 is of a self-inclusive enclosure design that provides environmental control and nutrient support for growth and maintenance of live cells. Growth-supporting environment 10 includes a lid 12 that provides access to, and sealing of, the enclosure; side portions 14; end portions 16: and a bottom portion 30. Growth-supporting environment 10 is constructed of a rigid and stable material including, but not limited to, e.g., aluminum; surgical steel; stainless steels; polystyrenes, fluoropolymers (e.g., TEFLON®), including combinations of these materials. Growth-supporting environment 10 provides a sterile, non-toxic, environment for growth of live cells from at least one biological organism introduced thereto. Growth-supporting environment 10 also provides for containment of vital fluids and nutrients, as well as environmental gases that are introduced to, and exchanged from, the enclosure. In the figure, growth-supporting environment 10 also includes a heater 22 that provides temperature modulation within the enclosure. Location of heater 22 is shown positioned on an end portion 16, but is not limited thereto. Growth-supporting environment 10 also maintains control over various other environmental factors including, e.g., humidity, as described further herein. Growth-supporting environment 10 is preferably of a rectangular shape, but shape is not limited. Lid 12 further includes an optically transparent view window 20 for viewing the interior of the enclosure vessel. Growth-supporting environment 10 also includes an ATR substrate of a flat plate design, mounted on bottom (base) portion 30, described further in reference to FIG. 2b. Growth-supporting environment 10 (enclosure) further includes various ports 18 that allow for introduction and exchange of fluids and gases, and/or coupling of various devices and sensors, e.g., for monitoring the internal environment of the enclosure in real time. Ports include, but are not limited to, e.g., input and output ports, sensor ports, fluid ports, gas ports, and device and instrument ports. In the figure, growth-supporting environment 10 is configured with two ports 18 of a quick disconnect coupling type positioned on end portion 16 that maintain the sterile environment within the enclosure. Number, position, and type of ports are not limited. For example, ports can be introduced at various locations of the enclosure vessel to provide control of, e.g.; atmospheric gases (e.g., $CO_2$, $O_2$); humidity; non-biological particulates and biological particulates [e.g., in conjunction with use of a high efficiency particulate air (HEPA) filters]; pressure, and like environmental factors. Ports introduced, e.g., in the lid or side portions (walls) of the enclosure vessel allow for introduction of devices and sensors (e.g., $O_2$ and $CO_2$ sensors), as well as introduction and removal of fluids, including, e.g., nutrient media or other constituents (e.g., via fluid transfer pipette). Ports can also be used to introduce toxins, drugs, or other reagents to the enclosure vessel without having to decouple the enclosure from the FTIR analysis instrument. The ATR substrate thus remains aligned with the FTIR during a critical time of an experiment, e.g., at the beginning of a drug exposure or dosing period. This capability also prevents unintended agitation of cells growing on the ATR substrate or within the fluid media within the enclosure.

Figure 2B:
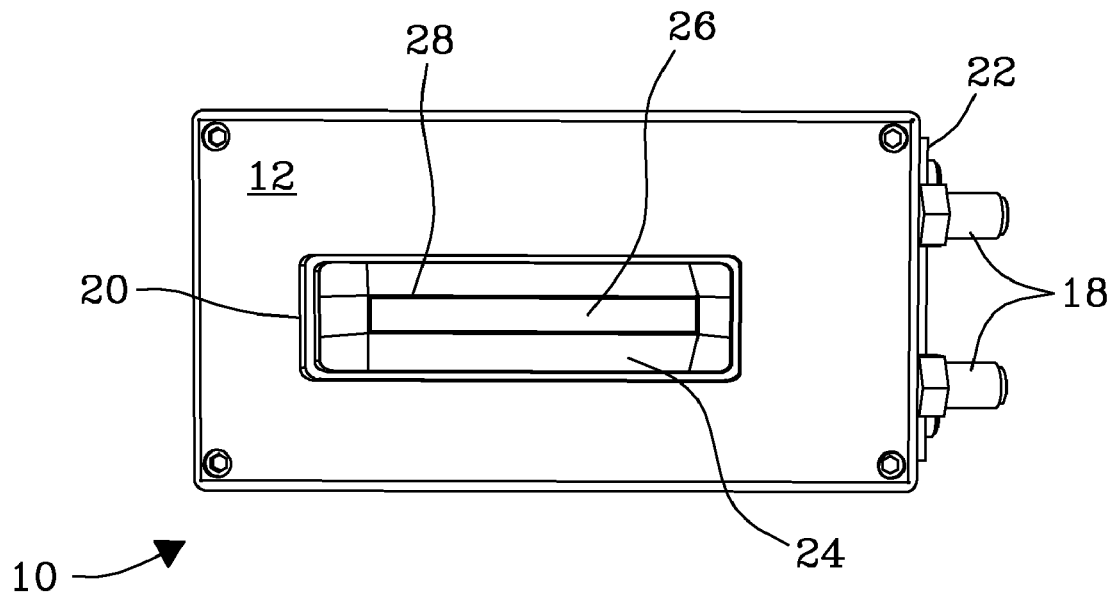

FIG. 2b shows a base portion 30 of growth-supporting environment 10. Growth-supporting environment 10 includes an ATR substrate 26 that is mounted to an ATR plate 32 in base portion 30. ATR substrate materials include, but are not limited to, e.g., zinc selenide (ZnSe); zinc sulfide (ZnS); germanium (Ge), amorphous IR transmitting glasses (AMTIRs), including combinations of these materials. ATR plate 32 surrounds and mounts ATR substrate 26 within the enclosure vessel and is constructed of a rigid and stable material (e.g., stainless steel). Size and position of ATR substrate 28 are determined by dimensions of enclosure 10 needed for proper alignment with the FTIR instrument during operation. Dimensions (e.g., length, thickness) of ATR substrate 26 are selected to align with selected mirrors that direct an incoming (incident) radiation beam (e.g., near-IR, mid-IR, far-IR, THz, (mm)-wave, etc.) into the ATR substrate or can further direct a reflected radiation beam (e.g., raman). As will be understood by those of skill in the spectroscopic arts, radiation beams may be active at preselected wavelengths in a single spectroscopic venue (e.g., in the IR), or may be active at preselected wavelengths in more than one spectroscopic venue (e.g., in both the IR and/or Raman). Thus, no limitations are intended by descriptions and illustrations to preferred embodiments herein directed to the IR venue. The IR beam provides sampling locations along the ATR substrate surface that are defined by various parameters such as IR wavelength ($\lambda$), and critical angles ($\theta_c$), described further herein. ATR substrate 26 is detachable from enclosure 10, which allows it to be cleaned or sterilized, e.g., by soaking in 70% ethanol, or in a manner that does not require autoclaving. In the figure, ports 18 and heater 22, described previously herein, are shown positioned on end portion 16, but location is not limited. A seal 28 infernal to enclosure 10 surrounds ATR substrate 26 to prevent leakage and loss of fluids from enclosure 10. Cells growing on the ATR substrate can be viewed and examined through the ATR substrate with IR microscopy using, e.g., a transmission or inverted optical microscope or instrument. Confluency of cells can determined quantitatively, semi-quantitatively, or qualitatively by evaluating the coverage of cells on the ATR substrate. The term "cell confluency" means the degree of coverage or proliferation of cells on the ATR substrate. For example, cell confluency can be quantified (e.g., a lower water noise represents a higher confluency) using FTIR absorption measurements that can be calibrated to a maximum/optimum confluency in a selected cell line. A degree of confluency of >95% is preferred in order to maximize cellular interaction with an evanescent wave that probes the cells, and to reduce background interference due to absorbance from selected media, e.g., a water-based medium, but is not limited thereto. For example, a minimum cell confluency that permits sufficient cellular interaction with an evanescent wave can also be used. The term "evanescent wave" as used herein means a near-field standing wave of infra-red radiation that is formed at the boundary (interface) between two "media" that each have different properties with respect to wave motion. Evanescent waves have an intensify that exhibits exponential decay as a function of distance from the interface at which it is formed. Evanescent waves are most intense within a distance of about one-third of a wavelength from the surface at which they are formed. An optical microscope can be coupled to the growth-supporting environment (enclosure vessel) for viewing and monitoring of cells in real time. Selection of the optical instrument depends on whether the ATR substrate is transparent in the visible and/or IR.

Figure 2C:
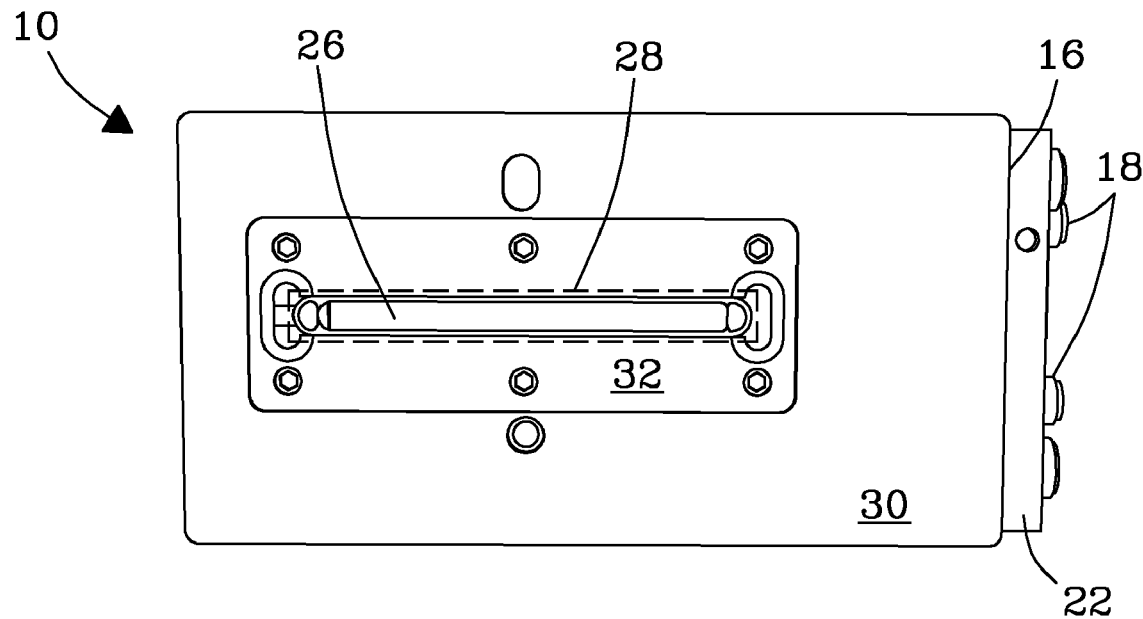

FIG. 2c is a top view of growth-supporting environment 10 (enclosure vessel). In the figure, lid 12 includes an optically transparent view window 20 through which the interior of enclosure 10 can be viewed. Two (gas/vapor) ports 18 and a heater 22 are shown positioned on end portion 16, but components and position are not limited thereto. Growth-supporting environment 10 further includes a media trough 24 located immediately superior to ATR substrate 26, which surrounds the substrate in enclosure 10. Trough 24 holds a preselected volume of a cell nutrient or fluid medium in contact with cells that affix to ATR substrate 26. The trough has at least one surface (wall) with a preselected pitch or angle that channels fluids back into the trough that may have been splashed onto cell surfaces during transport of the enclosure vessel to the FTIR instrument. Dimensions, volume, and pitch (angle) of the surfaces (walls) of trough 24 are not limited, in the preferred embodiment, trough, includes at least one surface with a pitch or angle selected in the range from about 30° to about 90°, but is not limited thereto, A seal 28 mounts between trough 24 and ATR substrate 26, and surrounds ATR substrate 26 to prevent leakage of fluids and/or nutrient media from growth-supporting environment 10 that nutrient the live cells within the enclosure. Seal 28 is preferably of an o-ring type made of a gasket material including, but not limited to, e.g., fluoropolymers (e.g., TEFLON®), rubbers, or an epoxy, but seal design is not limited. Seal 28 must be non-toxic to cells introduced to the enclosure as cells are in contact with the seal. Cells can be grown on the ATR substrate using a functionalization layer, as described further herein. Growth-supporting environment 10 is preferably aligned with the FTIR instrument only once prior to start of an experiment, which allows the cells to remain undisturbed for the duration of the experiment. Optical drift that occurs during experiments is corrected for using instrument software, as described further herein.

Figure 2D:
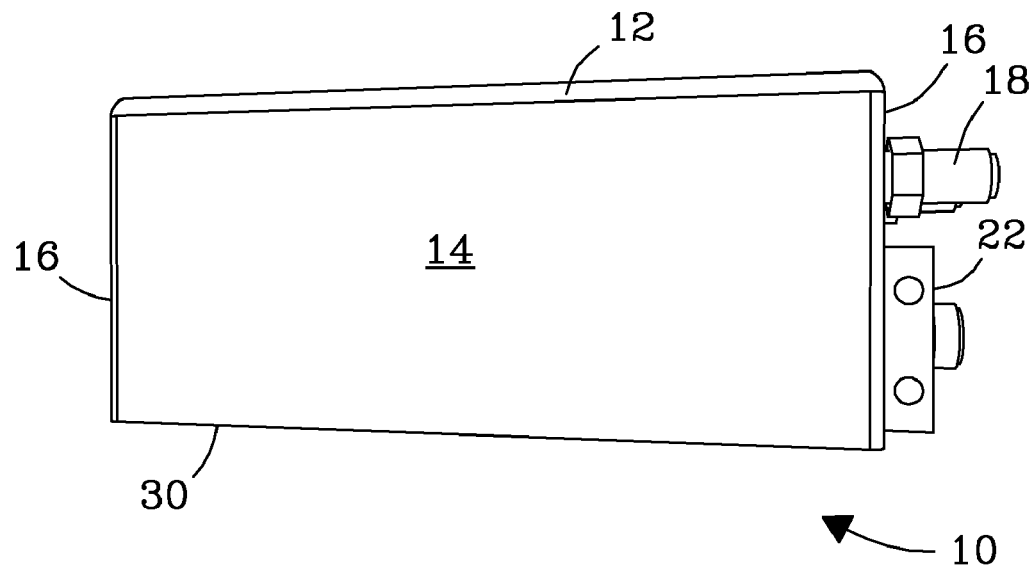

FIG. 2d shows a side view of growth-supporting environment 10 (enclosure vessel) of ATR-FTIR device 100. In the figure, enclosure 10 includes at least one side portion 14, two end portions 16, a lid 12, and a bottom portion 30. As described previously, enclosure 10 further includes ports 18 for exchange of environmental gases and fluids, and a heater 22 that provides temperature modulation and control for the enclosure vessel. In the instant embodiment, heater 22 is shown coupled to side portion 16, but the device is not limited thereto. For example, in other embodiments, heater 22 can be a free standing unit, or can be integrated (attached to) with growth-supporting environment 10, e.g., in a different location, e.g., to the base portion of the enclosure. Thus, no limitations are intended.

Figure 2E:
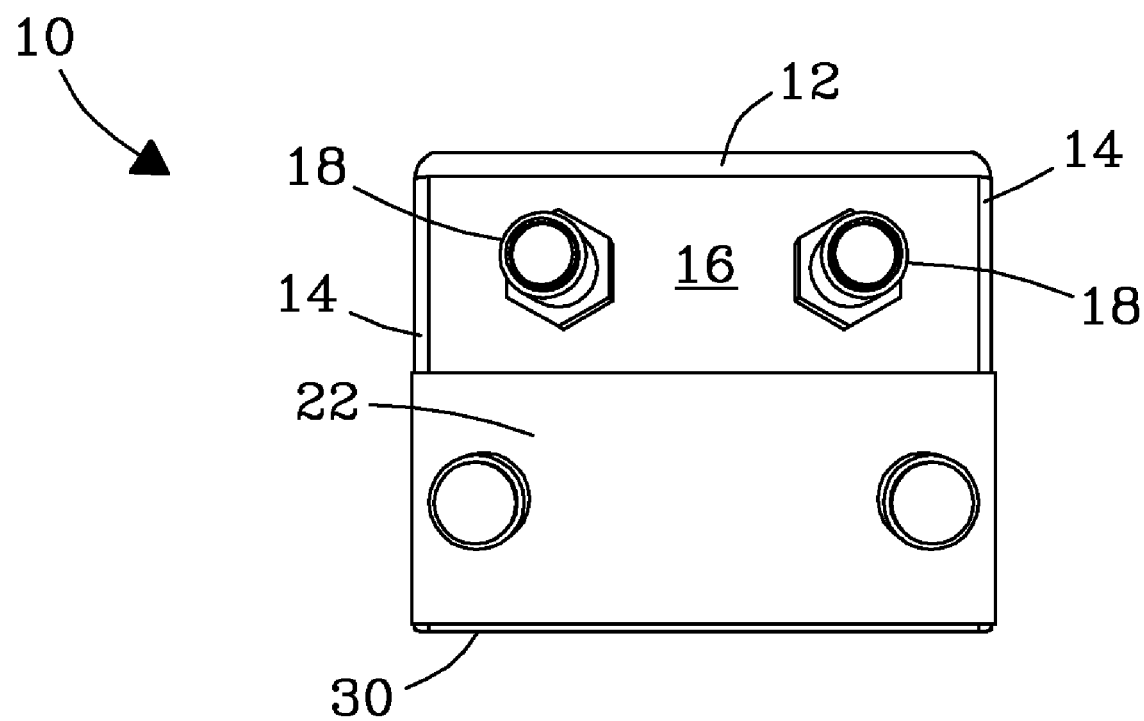

FIG. 2e shows an end view of growth-supporting environment 10 (enclosure vessel) of ATR-FTIR device 10. In the figure, enclosure 10 includes at least one end portion 16, two side portions 14, a lid 12, and a bottom portion 30. Growth-supporting environment 10 includes ports 18 that provide for exchange of environmental gases and fluids, and a heater 22 that provides temperature control for the enclosure, including, e.g., the temperature of the nutrient medium that maintains cell growth over a sustained period. The enclosure is constructed of a material (e.g., metal) preselected to provide uniform heat distribution and conduct heat efficiently. Heaters uniformly heat, e.g., the trough, the nutrient media in the trough, the ATR substrate, and other associated components to maintain a desired temperature within the enclosure vessel for an extended time period (e.g., hours or days). Heaters and heating devices include, but are not limited to, e.g., water jacket heaters, oil heaters, silicon heaters, thermoelectric heaters (e.g., Peltier devices), or other heaters. In the exemplary design, a silicone heater is shown, but is not limited thereto. A built-in thermocouple (not shown) provides precise temperature measurement and control. Seal and gasket materials shield the exposed region of the silicone heater from the cell nutrient medium. While heater 22 is shown attached to side portion 16, location on the device is not limited thereto. For example, heater 22 can be positioned in a location within, outside, or separate from growth-supporting environment 10 (enclosure vessel), or can be integrated (attached) to, e.g., base portion 30 of enclosure vessel 10 to provide ideal temperature modulation and control. All positions and configurations for heaters selected by those of skill in the art in view of this disclosure are within the scope of the invention. Thus, no limitations are intended. Growth-supporting environment 10 (enclosure vessel) is of a self-inclusive design, meaning it is configured with an ATR substrate 26 in a single device. Thus, once coupled to, and aligned with, an FTIR, the growth-supporting environment can remain in place at all times. Cells are kept under normal growth conditions and therefore the device provides for continuous, real-time monitoring of cells in vitro. Cells are grown and maintained under normal growth conditions in the fluid medium within enclosure vessel 10 and further monitored in vitro. Cells within enclosure vessel 10 can be exposed to different kinds of stresses (e.g., chemical, thermal, and radiological), and the interplay of such stresses on the cells can be evaluated. All equipment components as will be contemplated by those of skill in the art in view of the disclosure are within the scope of the invention. No limitations are intended.

Depth of Penetration

Depth of penetration ($d_p$) of an evanescent wave is given by Equation [1], as follows:

$$d_P = \frac{\lambda_0}{2\pi\sqrt{n_1^2\sin^2\theta_1 - n_2^2}} \quad [1]$$

Here, ($n_1$) is the index of refraction of the ATR substrate material; ($n_2$) is the index of refraction of the specimen material (e.g., live cells in contact with the ATR substrate in the fluid medium); ($\lambda_0$) is the wavelength of IR source; and ($\lambda$) is the angle of reflection of an evanescent wave, described further herein. Selected ATR substrate materials preferably have one or more of the following properties: a) are water insoluble; b) exhibit a low absorbance in the wavelength range of interest (e.g., near-IR, mid-IR, tar-IR, THz, mm-wave; Raman); c) are durable; and d) are machinable as a solid. TABLE 1 compares index of refraction values and other optical information for various ATR substrate materials.

TABLE 1

Optical Information for ATR Materials and Water.

| MATERIAL | ATR RANGE λ (μm) | ATR RANGE $\tilde{v}$ (cm$^{-1}$) | Index of Refraction n (λ) |
|---|---|---|---|
| Water | — | — | [1] |
| ZnS (multispectral) | 0.588-10.5 | 17000-950 | [2] |
| ZnS (CVD) | 0.588-10.5 | 17000-950 | [2] |
| ZnSe | 0.500-15.4 | 20000-650 | [2] |
| AMTIR-1 | 0.909-11.9 | 11000-840 | [2] |
| Si | 1.20-6.67 | 8300-1500 | [2] |
| Ge | 1.81-14.8 | 5500-675 | [2] |

[1] Handbook of Optical Constants of Solids, Edited by: Edward D. Palik, Elsevier, 1998.
[2] Harris, D. C., "Materials for Infrared Windows and Domes" in SPIE-The International Society for Optical Engineering, (1999).

Figure 3A:
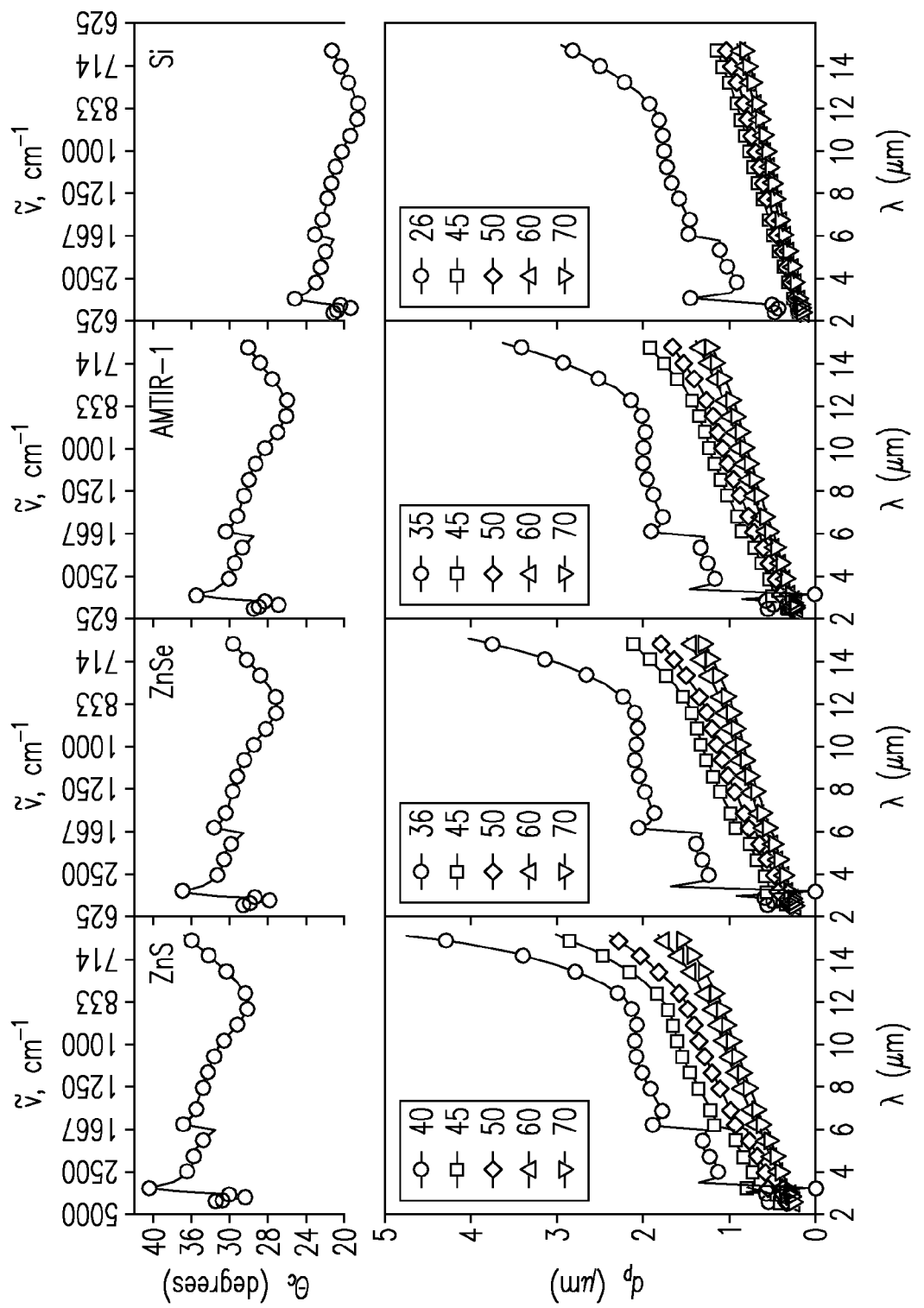
FIG. 3a compares depth of penetration ($d_p$) values as a function of wavelength ($\lambda$) for various ATR substrate materials against critical angles ($\theta_c$) as a function of wavenumber ($\tilde{v}$).
Figure 3B:
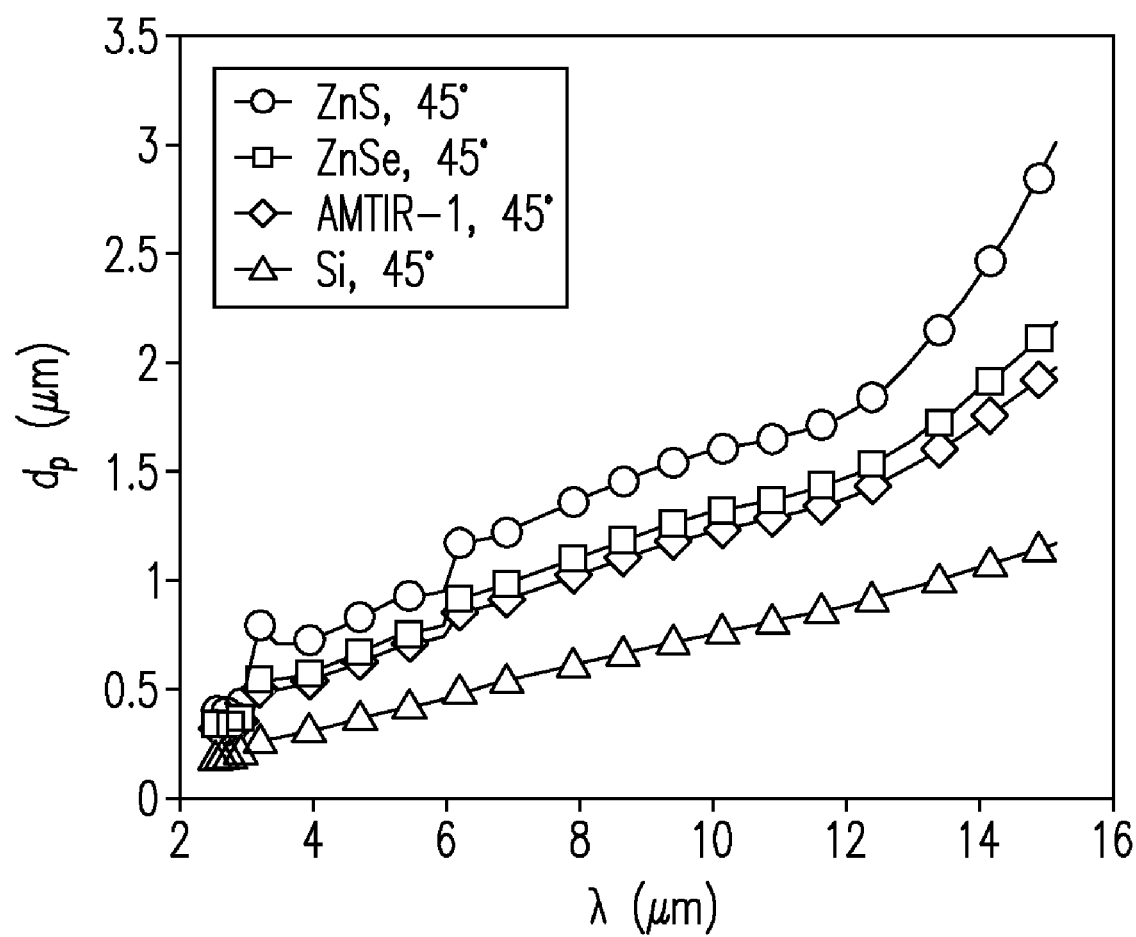
FIG. 3b shows depth of penetration ($d_p$) values for various ATR substrate materials at a reflection angle ($\theta$) of 45° as a function of wavelength ($\lambda$).

Depending on the applications or intended uses, an ATR substrate material can be selected with a suitable transparency range. Depth of penetration of the evanescent wave is directly dependent on the critical angle ($\theta_c$) between an ATR substrate material and, e.g., water in the nutrient medium (low index medium), which varies as a function of wavelength, λ (and wavenumber, $\tilde{v}$). FIG. 3a compares dependence of depth of penetration ($d_p$) values on wavelength (λ), wavenumber ($\tilde{v}$), and incident reflection angle (θ) for various ATR substrate materials suitable for use in conjunction with the invention. Values for the index of refraction (n) as a function of wavelength (λ) are taken from TABLE 1. Critical angle ($\theta_c$) values as a function of λ and $\tilde{v}$ are also included for these materials in contact with water, in the figure, like (θ) values were used for ail plots in addition to a (θ) value very close to the critical angle ($\theta_c$) maximum for each material over the wavelengths (λ) presented. FIG. 3b shows depth of penetration ($d_p$) values for various ATR substrate materials at a reflection angle (θ) of 45°. In a preferred embodiment, the ATR substrate is a zinc selenide (ZnSe) crystal. ZnSe has high transmission (~70%) in the mid-IR (2.5 μm to 25 μm) range. ZnSe is also a durable material (e.g., hard) that can be used at a wide range of temperatures, e.g., above room temperature. In addition, ZnSe can also be cleaned and sterilized in preparation for cell growth with various solvents including, e.g., 70% ethanol. ZnSe also exhibits a low absorbance value at a low wavenumher region (~650 cm$^{-1}$). ZnSe is also transparent in the visible light region, which allows for optical monitoring and measurement of cell growth and viability during cell-growth experiments using, e.g., transmitted visible light. Reflected light is also an option for most optical microscopes. ZnSe is also insoluble in water, a preferred base component of the nutrient medium used to nourish and maintain cells in a viable state. ZnSe is also compatible with cells tested in conjunction with the invention (see EXAMPLE 1 below), Cells are viable on the ZnSe crystal up to several days. The cell lifetime in the enclosure vessel depends on the selected growth reagent, nutrient medium, humidity, environmental gases, temperature, pressure, and other associated environmental factors. Optimization of these factors can be expected to maximize longevity of cells being investigated in conjunction with the invention. Presently, average cell lifetimes are $\geq$24 hours.

Collection of Live Cell Data

ATR Mode

Figure 4:
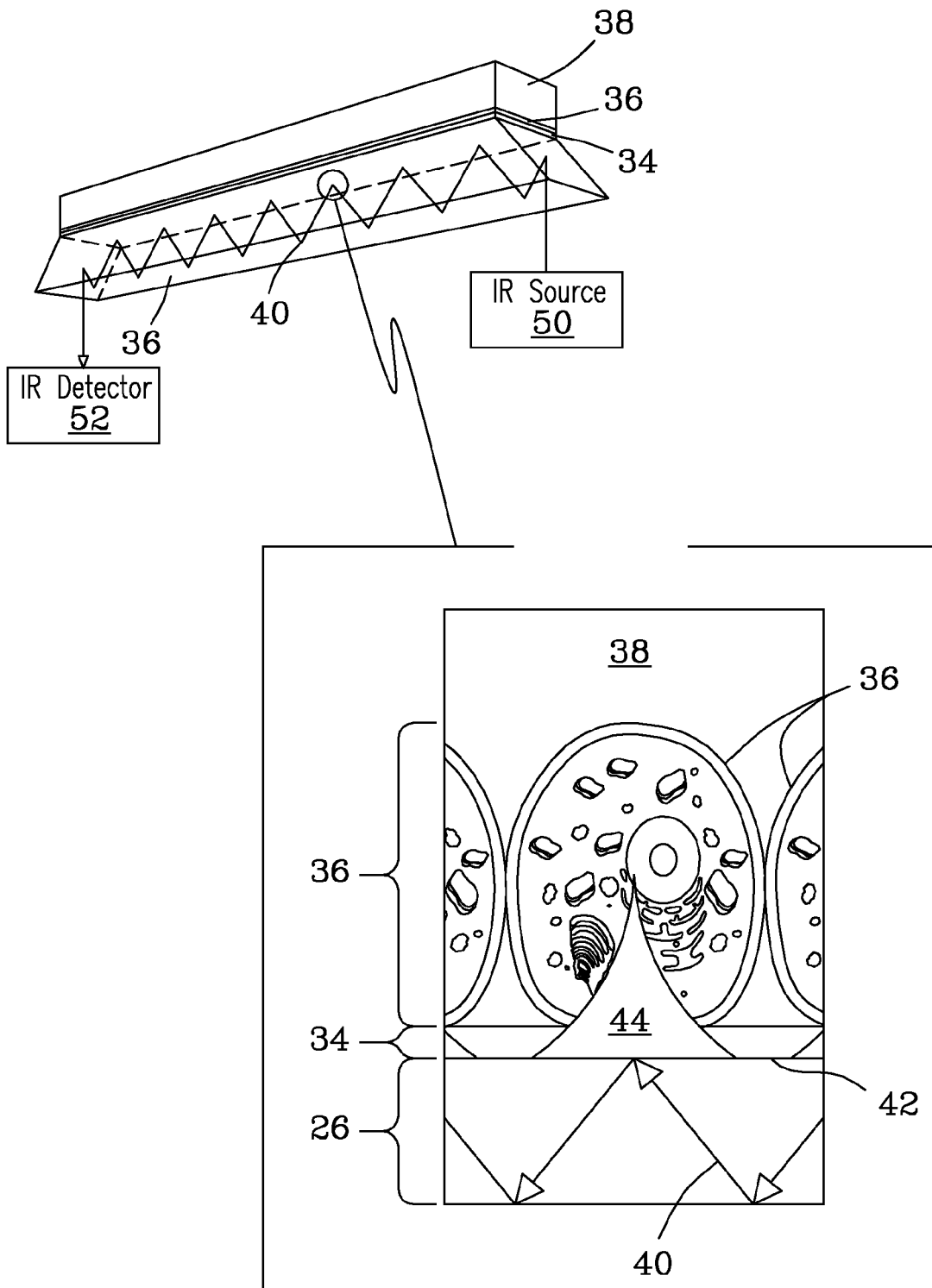
FIG. 4 is an expanded view of an ATR substrate that includes a functionalization layer and sample (cell) layer that shows the penetration of an evanescent wave into the cell layer.

FIG. 4 shows an ATR substrate 26 that includes a functionalization layer 34 and cells 36 that allow cell measurement and collection of live-cell data. When used, functionalization layer 34 has a thickness selected in the range greater than or equal to about 0.5 nm to about 1 μm, Functionalization layer 34 can include a structured growth material (e.g., FIBRONECTIN®) composed of, e.g., structured fibers and a cell growth reagent that is applied to ATR substrate 26 to promote cell growth, cell layer convergence, cell adhesion, and cell function. A layer of live cells 36 can be grown atop functionalization layer 34 to a preselected confluence (coverage). A confluence greater than 40% is preferred. Confluences up to 100% can be achieved depending on the selected cell type. Cells 36 grown on functionalization layer 34 are fed by a nutrient medium 38 that remains in contact with the cells throughout their lifetime in the growth-supporting environment (enclosure vessel) described previously herein (see discussion FIGS. 2a-2e). In operation, an IR beam 40 from an IR source 50 is transmitted through ATR substrate 26. An evanescent wave 44 is generated when IR beam 40 penetrates through an interface 42 (interfacial surface) located between ATR substrate 26 and functionalization layer 34. Evanescent wave 44 can penetrate through the functionalization layer 34, the cells 30 grown on the functionalization layer 34 attached to the ATR substrate, as well as the nutrient medium 38 located above the cells in the enclosure vessel. The wave interrogates and carries information obtained about the cells. The IR beam reflects infernally along the length of the ATR substrate until it exits. Detection is provided by an IR detector 52. Cells 36 and nutrient medium 38 have a low index of refraction being largely composed of water (e.g., water index of refraction, $n_{H2O}$=1.333). Depth of penetration can be increased by going, e.g., to an ATR substrate having a lower incidence angle (i.e., close to $\theta_c$), or an ATR substrate with a low-index of refraction closer to that of the low-index medium, i.e., H$_2$O. The interface surface does not prevent the gathering of, e.g., vibrational and other IR data about cells 36 in the cell layer. Depth of penetration ($d_p$) is a measure of the ability of IR beam 40 to probe cells 38 of interest as a function of time. In the preferred embodiment, the ATR substrate is a horizontal ATR crystal composed of ZnSe, ATR substrate 26 dramatically reduces interferences associated with IR absorbing properties of water and media influences in live cell measurements. The ATR substrate also has the advantage of capturing information from the evanescent wave that passes through the cell monolayer. ATR substrate 26 is preferably beveled or tapered at the ends (edges) of the substrate to include a angle typically ranging from about 30° to about 80°, or as otherwise limited by the critical angle with respect to the (e.g., planar surface of) interface 42, but is not limited thereto. This critical angle provides a preselected incidence angle for introduction of IR beam 40 to the ATR substrate 26. In one embodiment, the ATR substrate has edges planed at an angle of 45° relative to the substrate surface. While a 45° substrate is shown, angles are not limited thereto, in the figure, as IR beam 40 reflects internally along the upper surface of the ATR substrate 28, evanescent wave 44 penetrates info cells 36 and/or medium 38, in the instant embodiment, the ATR substrate 26 is a 12-bounce type, meaning the evanescent wave penetrates info cells 36 at 12 independent locations along the surface of the substrate where the cells are growing, providing 12 sampling locations, but number of sampling locations is not limited thereto. For example, as described above, a substrate with 30° or 60° edges may he used which can change the number of internal bounces. In addition, number of reflections (bounces) in the crystal is not limited. For example, a maximum number of bounces that produces a maximum number of sampling locations can be produced. Alternatively, fewer bounces can be used depending on the intended application. No limitations are intended. Thus, while a 12-bounce ATR substrate is described, the invention is not limited thereto, in other embodiments, thinner ATR substrates can be used to change (e.g., increase) the number of bounces, e.g., at the same incidence angle (θ). No limitations are intended. While a description of live cell tests that require adhesion to the ATR substrate have been described, e.g., with reference to a functionalization layer, the invention is not limited to experiments that require cell adhesion on the ATR substrate. Various tests can be conducted that do not require adhesion of cells to the ATR substrate. For example, cell proteins and other molecules can be monitored in a suitable nutrient medium and changes assessed as a function of time. Thus, no limitations are intended.

Cell Growth on MB Substrate

Cells grow and function on the surface of the ATR substrate. The surface is benign and assists in cellular adhesion. Cell growth may be promoted by coating the ATR substrate with a growth promotion reagent. The surface layer functions have been previously described. Cells can be grown directly onto the ATR substrate atop the surface functionalization layer. Thus, the same cells and regions (i.e., total internal reflection locations) of the same cells are always analyzed during each IR-analysis event during the cell growth study during which IR data are collected. The configuration of the present invention is unique to the spectroscopic arts. The surface layer provides a functional interface between the ATR and the biological system. A range of surface chemistries and functionalization methods are envisioned. An exemplary surface layer includes a high molecular weight glycoprotein (e.g., FIBRONECTIN®, Sigma, St. Louis, Mo., USA) that is frequently used to promote cell attachment to a variety of substrates, but the invention is not limited thereto. Other surface chemistries that 1) adhere to the ATR substrate, 2) provide good cell adhesion, and 3) promote cellular growth and function can be used. Attachment of the functionalization layer to the ATR substrate may be performed using simple deposition, as is done with FIBRONECTIN®, or may involve another suitable method such as covalent bonding. Thus, no limitations are intended. For example, covalent bonding of a high-density monolayer can be advantageous since it provides a molecularly bound layer which is very stable and provides a high molecular density in the surface layer. High-density monolayers provide enhanced isolation of cells from the ATR surface, as well as isolation of the ATR surface from a nutrient, or fluid, medium. Isolation may result in better biological response and better ATR stability. A monolayer with a thiol base that will attach to chalcogenides typically used in ATR (i.e. ZnSe) and a surface group that promotes cellular function, e.g. quaternary salts or other biocompatible terminal groups is preferred, but is not limited thereto. Similarly, silanes may also be used to provide good monolayer formation on a compatible ATR substrate material in operation, the surface of the functionalization layer is exposed to cells and must promote adhesion and cellular function. A number of terminal surface chemistries are possible. TABLE 2 lists selected effective surface chemistries tested in conjunction with the invention that provide functionalization of the ATR surface in a suitable monolayer form.

TABLE 2

Effective Covalently-bound Surface Monolayer Chemistries for Cellular Adhesion and Viability on ATR Substrates.

| Terminal Surface Chemistry | Adhesion | Viability/Proliferation |
|---|---|---|
| Quaternary salt | Excellent | Yes |
| Carboxylic acid only | Suitable | Yes |
| Propyl | Suitable | Yes |
| Hexadodecane | Suitable | Yes |
| Fibronectin/polylysines | Excellent | Yes |

High-density monolayers including those that have monolayer defects passivated with small molecules (e.g., propyl, methyl head groups) provide better performance. Other surface chemistries such as those used to grow cells oh polystyrene plates, cellular growth gels, or other similar materials can be adapted as effective surface coatings, e.g., as monolayers or other surface coating formats.

Procedure for Cell Testing

Figure 5:
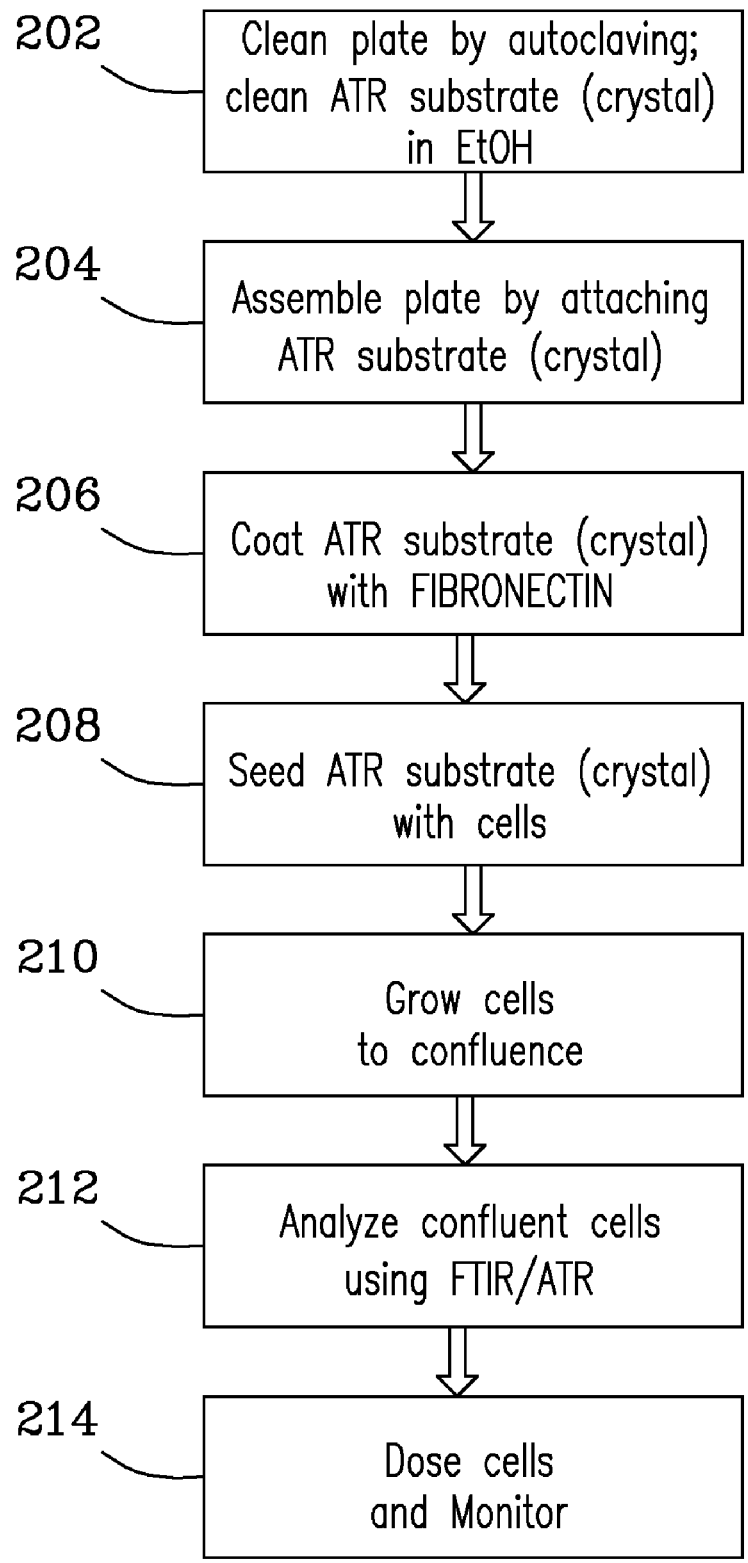
FIG. 5 is a schematic that shows exemplary steps for performing cell viability or cell perturbation tests, according to an embodiment of the process of the invention.

FIG. 5 is a schematic that shows a general process flow for performing a cell viability or cell perturbation test, according to an embodiment of the invention. {START}, First {step 202}, the ATR substrate(s) is cleaned. The ATR substrate must be cleaned using compatible reagents, e.g., 70% ethanol (diluted with DIW), but is not limited thereto. Autoclaving is a preferred cleaning method for the ATR substrate where compatible with the selected ATR substrate. Next {step 204}, the ATR substrate is mounted. Next {step 206}, the ATR substrate is optionally coated with a glycoprotein (FIBRONECTIN®) to promote cell attachment. Other surface chemistries with different surface properties or functionalities can be substituted (see TABLE 2). Next {step 208}, the ATR substrate is seeded with a preselected number of live cells, as will depend on physiology of the selected cell line. Next {step 210}, the cells are allowed to attach to the ATR Substrate and grow to a preselected confluency (coverage) level that ranges from preconfluent to confluent, which is dependent on the type of cell used. For example, C10-type cells can be grown to 100% confluency, whereas RAW246.7 cells can be grown to a confluency that is ~70-80%. Factors that affect confluency include, but are not limited to, e.g., type of cell; cell size; cell growth rate, cell configuration, and other factors that are dependent on the type of cell being used. Next {step 212}, the cells are analyzed stereoscopically to obtain a baseline measurement or assessment of the cell condition. Next {step 214}, the cells are dosed with a preselected stimulus (e.g., reagent, drug, or toxin) and monitored as a function of time. Next {step 216}, the cells are again analyzed spectroscopically for analysis and to determine cell condition. {END}.

Cell Viability Tests

Figure 6:
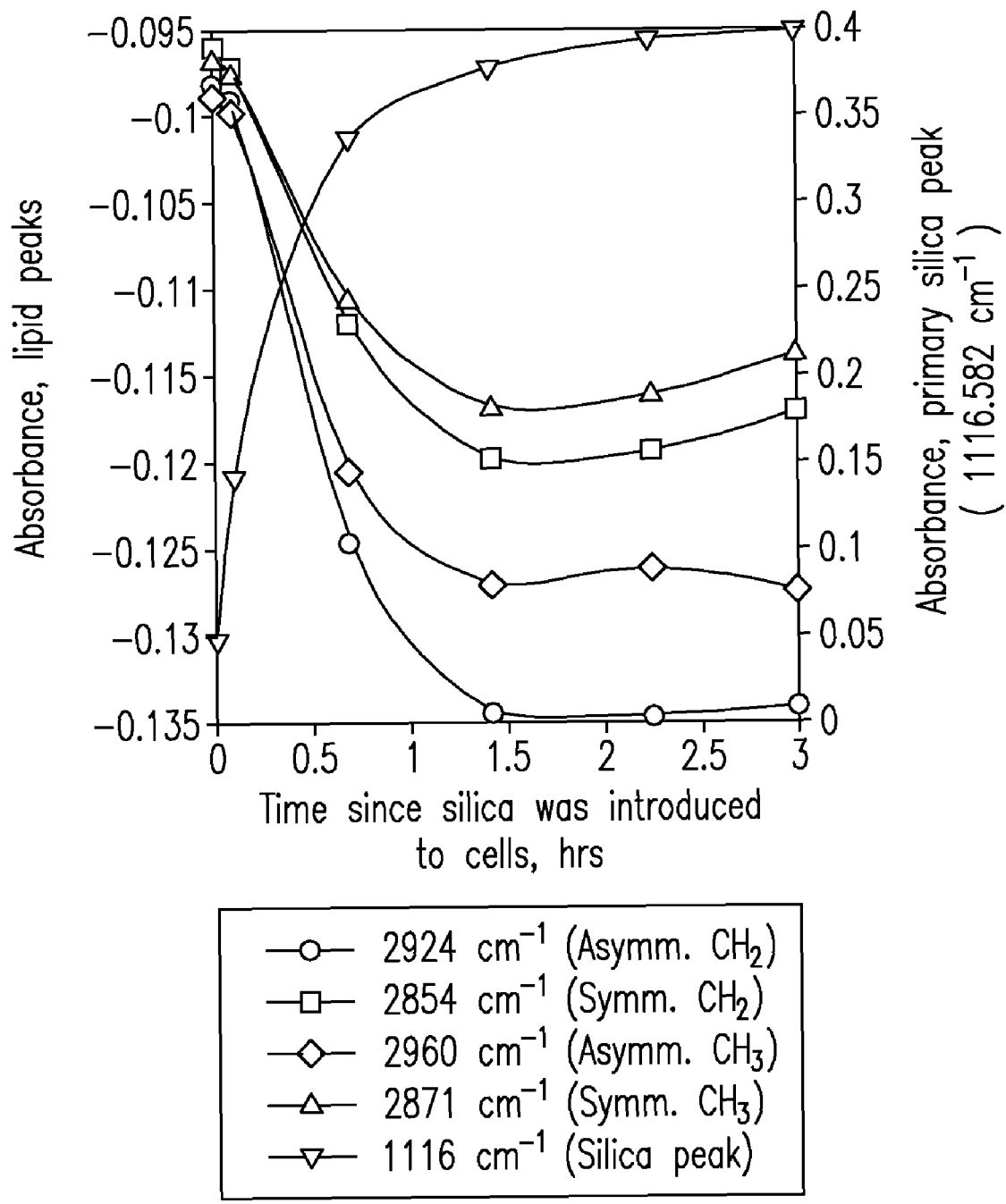
FIG. 6 shows infrared absorption spectra for cells treated with silica nanoparticles (a nanofoxin), showing changes in cell membrane peaks ($CH_2$ and $CH_3$) as a function of time.

Cell viability tests performed with the ZnSe ATR substrate will now be described, FIG. 6 shows infrared absorption spectra for cells (e.g., mouse epithelial cells) dosed with silica nanoparticles (a cellular toxin) as a function of wavenumber. The x-axis is "time", the two y-axes are "absorbance" and the different series are different wavenumber plots. In the figure, changes in absorbance peaks associated with the cell membrane (e.g., symmetric and asymmetric $CH_2$ and $CH_3$ peaks)

are compared against a primary silica peak as a function of time. Absorbance peaks for cell membranes are described, e.g., by Rigas et al. [Proc. Natl. Acad. Sci, USA, 87, pp. 8140-8144 (1990)]. Settling of nano-sized silica particles can be monitored by observing increases in IR absorbance at characteristic absorption frequencies. In the figure, a primary absorbance peak for silica is evident at ~1116 $cm^{-1}$. Cell response can be correlated with the arrival of the toxin, or the settling of particles near the surface of the cells. Data show the effect of adding silica nanoparticles (increasing absorbance) on the absorbance peaks associated with the cell membrane (decreased absorbance).

Figure 7A:
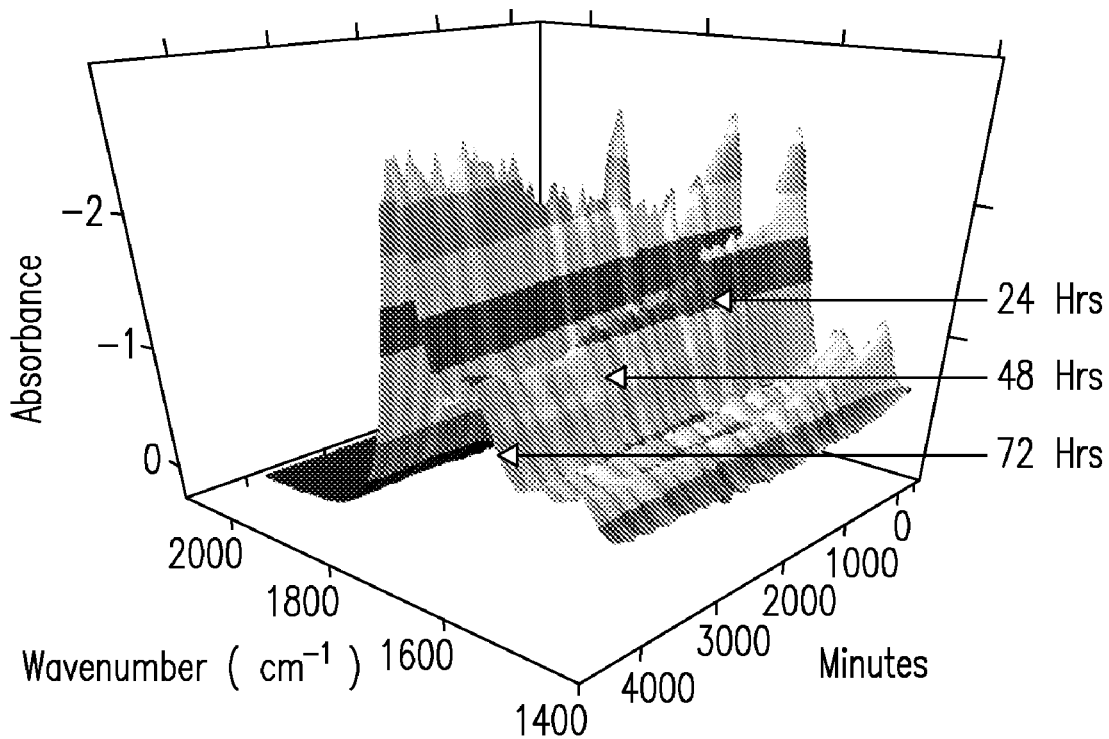
FIG. 7a shows a 3D infrared absorption spectrum of mouse cells that were grown on the ATR substrate that were treated with a tumor promoter and monitored after administration as a function of time over a 72 hour period.
Figure 7B:
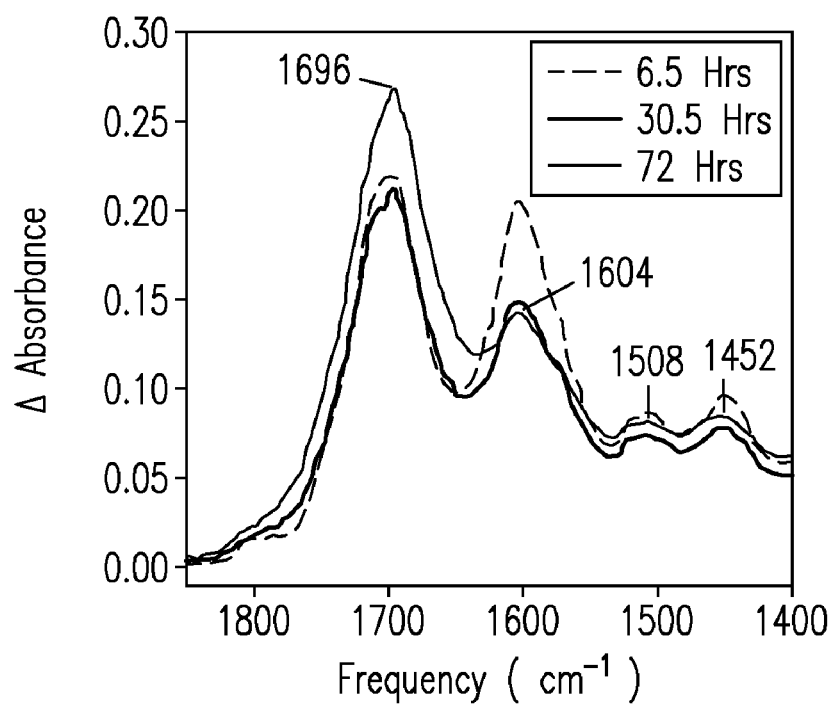
FIG. 7b shows three time slices taken from the spectrum of FIG. 7a that show changes in peak intensity over time.

FIG. 7a shows 3D infrared absorption spectra collected for mouse cells (e.g., carcinogenesis mouse endothelial model cells) grown on the ATR substrate that were treated with a tumor promoter, i.e., basic fibroblast growth factor (bFGF), Cells were monitored over a 72-hour period, with spectra collected at 15 minute intervals. Spent media was replaced with fresh media at 24-hour intervals. Cells were confluent at 24 hours and had attached to the ATR substrate. The tumor promoter bFGF was added at the 48-hour time point, FIG. 7b shows three time slices from FIG. 7a that were taken over the 72-hour period that illustrate changes in peak intensify over time, Amide bands observed at, e.g., 1696 $cm^{-1}$ and 1604 $cm^{-1}$ reflect protein conformation. The 1604 $cm^{-1}$ band also contains a broad water band which is observed at the 6.5 hour time point where there is greater media contact with the ATR substrate due to a non-confluent cell monolayer. At the 72-hour time point, the 1696 $cm^{-1}$ peak shows an increased intensity and has broadened. Results are attributed to cell death and demonstrate protein structural changes including, e.g., degradation of proteins released from dying cells. Tyrosine aromatic rings absorb in the 1508 $cm^{-1}$ region and the symmetric carboxylate stretching vibrations are reflected in the band at 1452 $cm^{-1}$. Overall, data reflect the ability to obtain spectra over a period of days which show the attachment of cells to the substrate and a response to perturbation.

System Configurations

The invention can be adapted for high-throughput analysis and operation. Various designs will now be described that scale from a single ATR substrate, that provide for rapid screening of live cells. Configurations include: 1) dual ATR substrate waveguide chamber designs, and 2) multiple ATR substrate waveguide chamber designs. The simplest rapid screening configuration includes more than one ATR substrate running in parallel.

Figure 8:
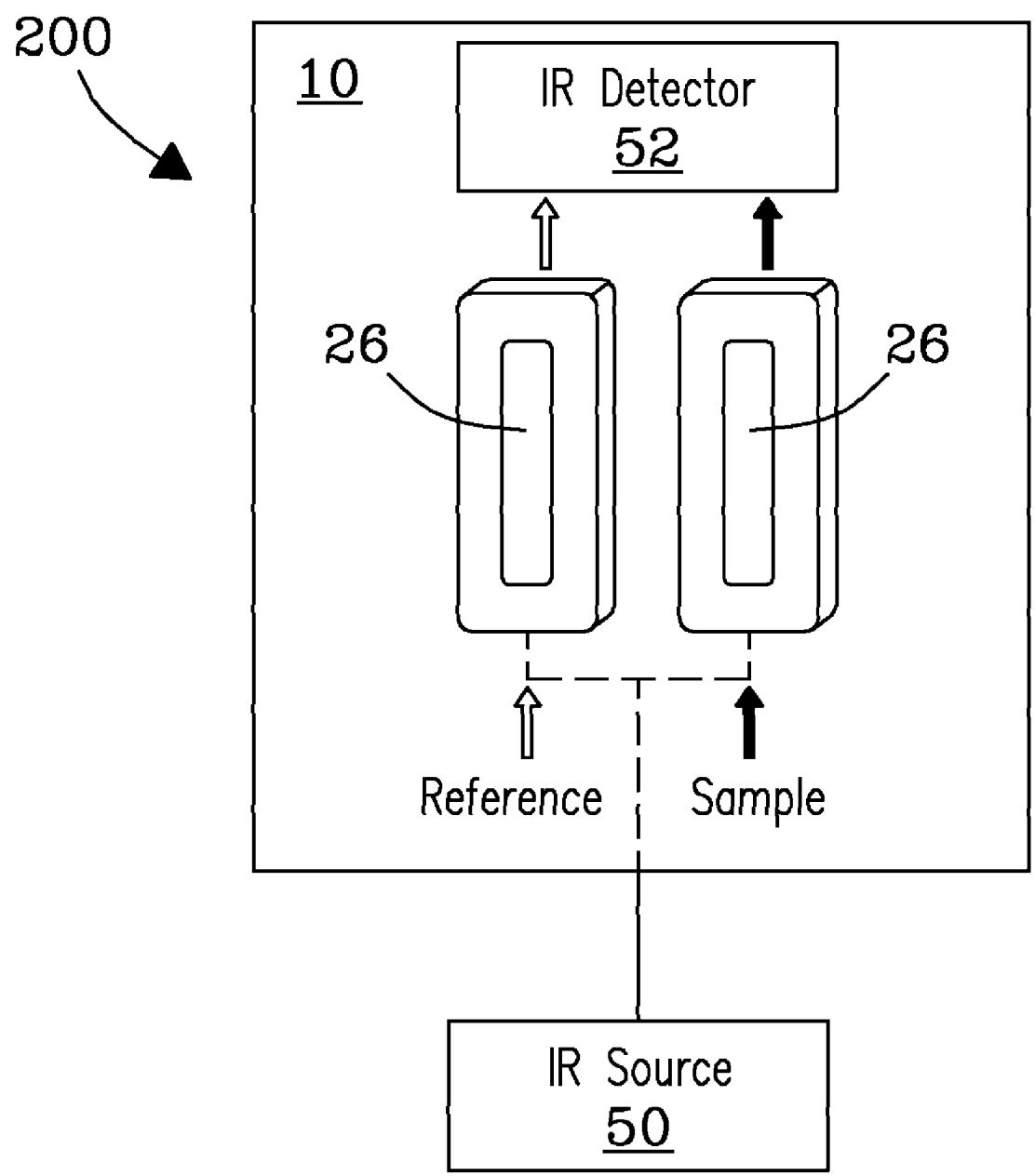
FIG. 8 shows an ATR configuration of a two-plate design for simultaneous screening measurements, according to an embodiment of the invention.

FIG. 8 shows a system 200 of a dual ATR substrate design that provides for simultaneous measurements of live cells, according to an embodiment of the invention. In the figure, enclosure vessel 10 includes one ATR substrate 20 or chamber that is used for analysis of a reference sample. A second substrate (waveguide) 26 or chamber is used for analysis of a test sample. Alternatively, each of the substrates can be used simultaneously to test different samples. A simple mirror (not shown) described further herein directs an IR beam info each of the ATR substrates and another mirror (not shown) directs light from the ATR waveguides to a single defector. For example, one ATR substrate containing untreated cells (reference sample) can be independently analyzed and monitored and compared against a second ATR substrate containing cells treated with a preselected reagent or drug (test sample). This configuration enables differential live-cell spectrometry that provides screening of, e.g., a regulatory sample against an unknown sample.

Figure 9:
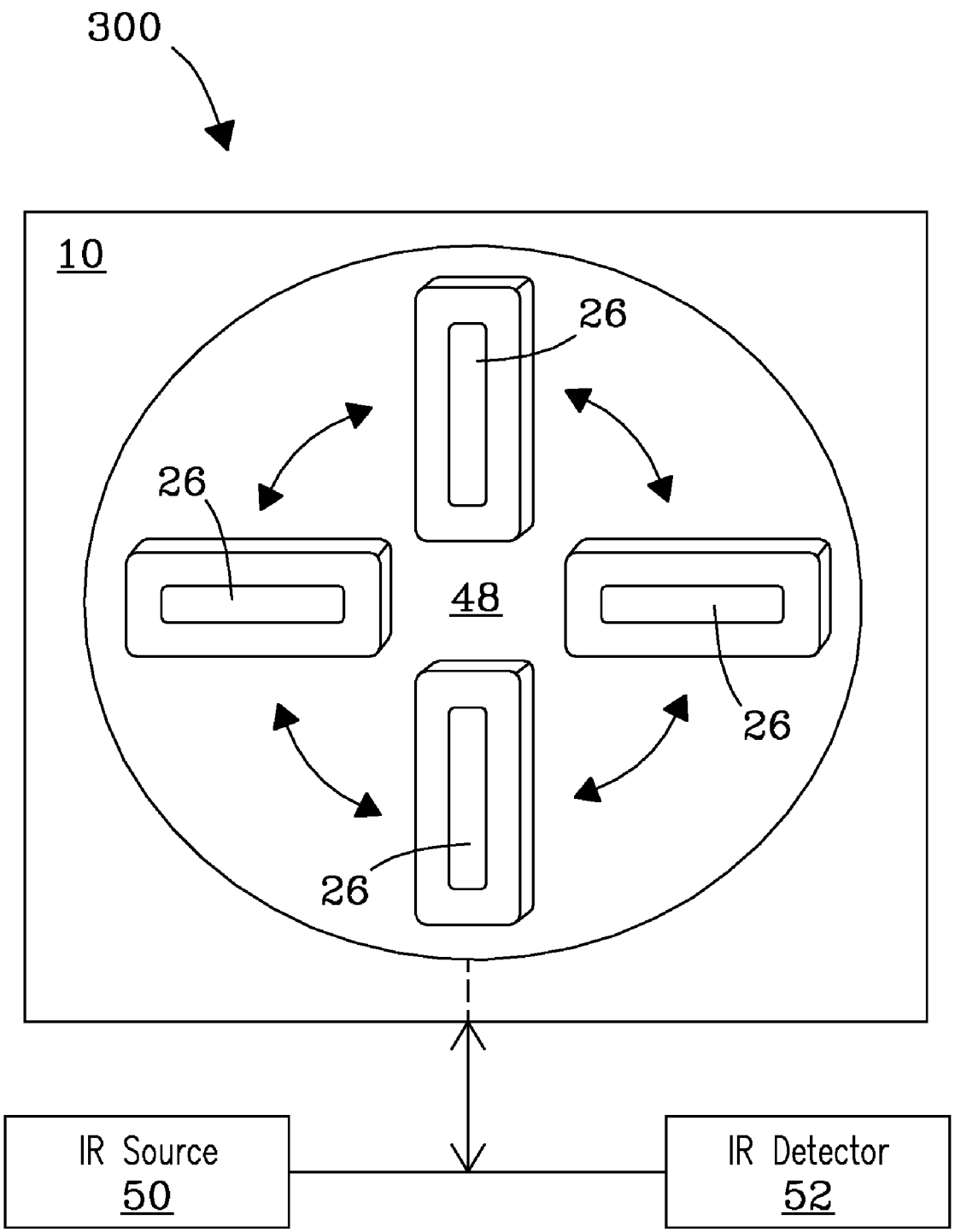
FIG. 9 shows a system of a multiple ATR substrate design that provides for simultaneous measurements of live cells, according to another embodiment of the invention.

FIG. 9 shows a system 300 of a multiple ATR substrate design that provides for simultaneous measurements of live cells, according to another embodiment of the invention. In the figure, enclosure vessel 10 includes four ATR substrates 28, but the design is not limited thereto. The instant design allows multiple live cell tests to be conducted simultaneously. Each of the ATR substrates 26 is mounted to a rotating stage or carousel as a chamber or well that allows for measurement of test samples, e.g., simultaneously or individually. The stage rotates to permit analysis of a different ATR substrate, e.g., in series. Each plate can be used to analyze a reference sample, a background sample, a regulatory sample, or other test material. Plane of rotation is not limited. For example, rotation can be about the horizontal plane, vertical plane, or combinations of these selected planes. In operation, each configuration can use a single IR source and multiple detectors; or, a single IR source and a single detector with individual pixels for each ATR substrate (waveguide); or, multiple IR sources with multiple detectors. Thus, no limitations are intended. Static system designs described further herein are preferred as physical movement of ATR substrate chambers can lead to agitation of cells on the ATR surfaces leading to artifacts in the IR measurement signals, individual ATR chambers (wells) can each employ an Identical experimental regimen, a different experimental regimen, or combinations of identical and different experimental regimens. The instant configuration utilizes a single FTIR instrument with a single set of optics (i.e., source and detector). A reference chamber can be included in the set of ATR substrate wells for purposes of comparison. In an alternate configuration, two or more substrates can be coupled and analyzed in parallel (e.g., side-by-side) at the same time using either the same or different optics (source/defector). In this embodiment, a reference sample can be run at the same time that a non-reference sample is being run. In an exemplary configuration, multiple samples can be run simultaneously to rapidly screen various or multiple toxic materials of a like or different kind, e.g., to test effect of the various materials in an equivalent time interval for comparison purposes, in an alternate configuration, multiple samples can be run with a single toxic material or stimulus on an equivalent time-scale (i.e., same start and end times) as replicates. In yet other embodiments, time-scale studies (i.e., different start and end times) of a single toxic material or stimulus can be run simultaneously. In yet other embodiments, an ATR substrate of a multiple-well design is envisioned as a component of a monitoring device or system that provides for simultaneous measurements of live cells. While preferred embodiments of the invention and method have been described, the invention is not limited thereto. All experimental approaches as will be contemplated by those of skill in the art in view of the disclosure are within the scope of the invention. Thus, no limitations are intended.

Figure 10:
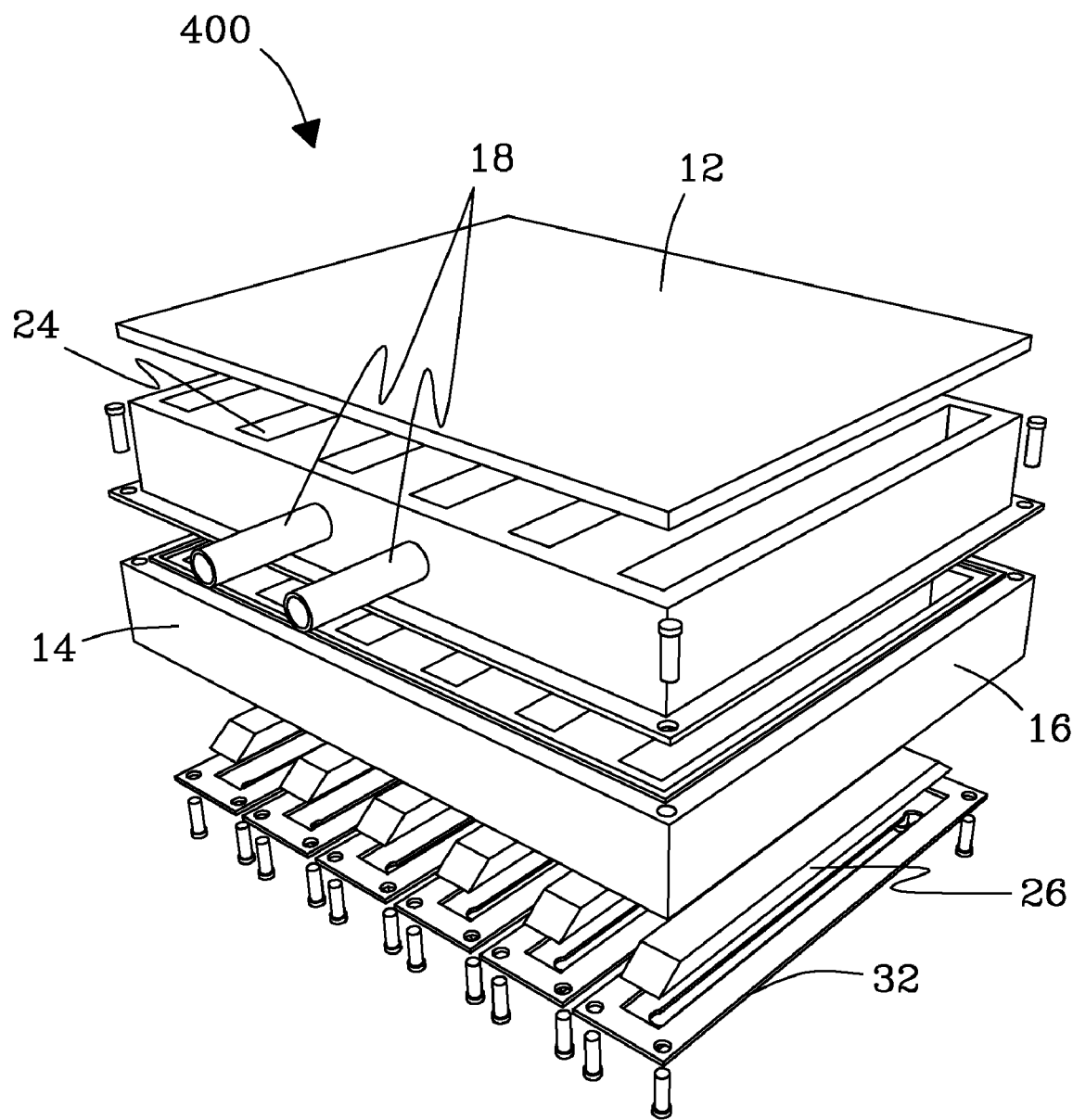
FIG. 10 shows an exploded view of an exemplary system of a multiple ATR chamber design, according to another embodiment of the invention.
Figure 11A:
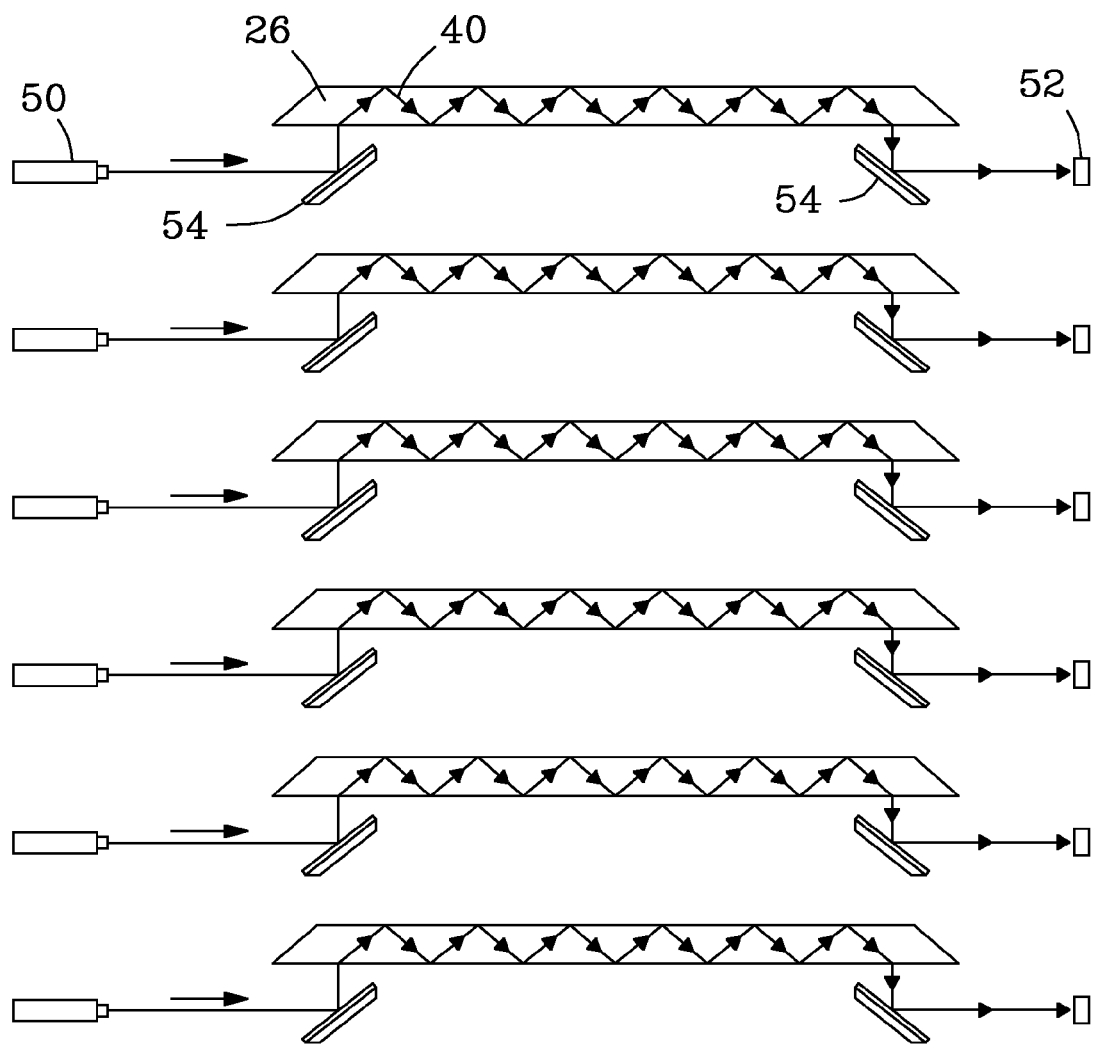
FIGS. 11a-11c present different IR source and detector (optical) configurations for use with systems that include multiple ATR substrates and chambers.
Figure 11B:
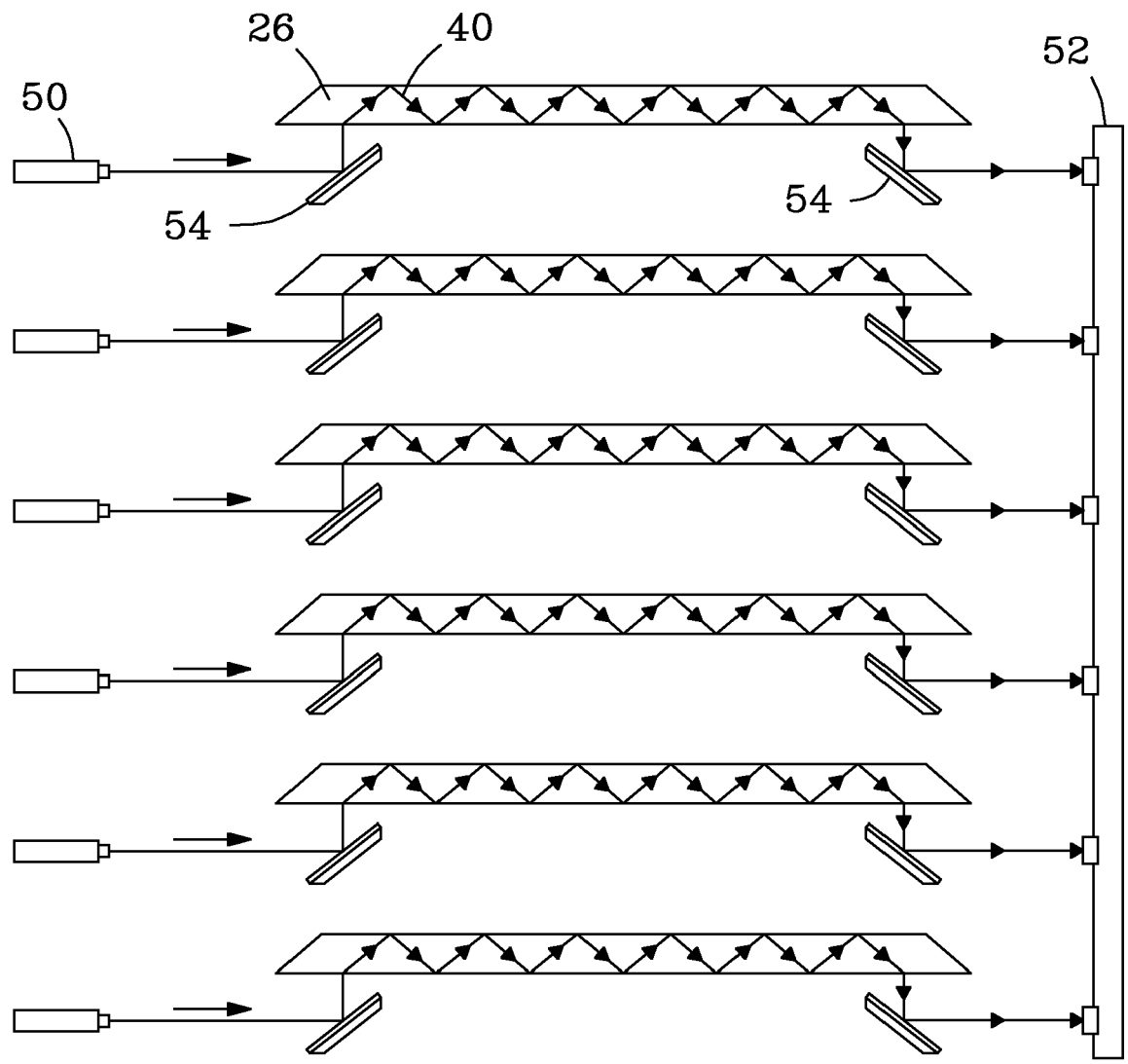
Figure 11C:
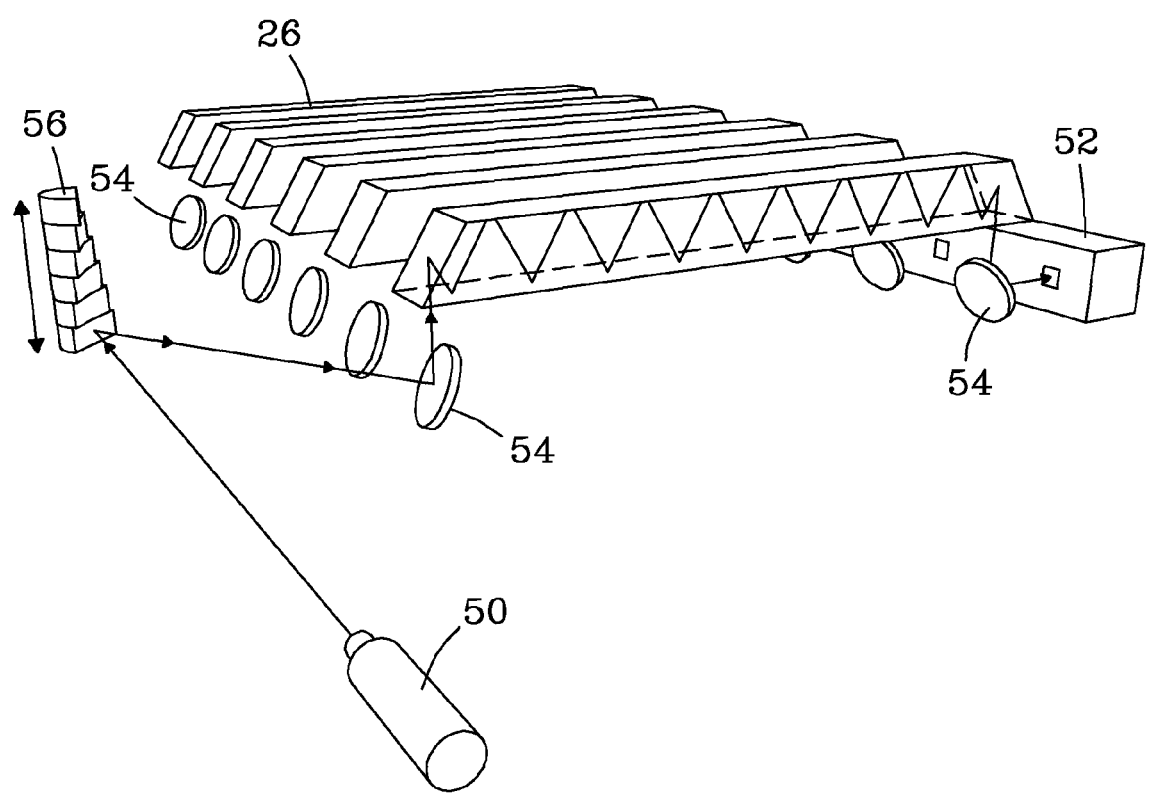

Multiple ATR substrate waveguide/chamber designs will now be described. FIG. 10 shows an exploded view of an exemplary system 400 of a multiple ATR chamber design, according to another embodiment of the invention, in the figure, six (6) ATR substrates In individual chambers are shown, but the system is not limited thereto. Performing experiments in a single integrated design using multiple ATR substrates and chambers is an effective system configuration given that the environmental headspace is the same for each integrated ATR substrates and chambers. This design can eliminate artifacts such as noise level attributed to variability in headspace conditions. As with single ATR waveguide chamber designs described previously herein, each of the multiple ATR chambers can be configured to move individually in order to align the ATR waveguides with, e.g., a single IR source and single detector. Again, movement of chambers is not ideal once experiments have been initiated as movement can agitate living cells on the surface of the ATR substrate causing artifacts. The instant design provides simultaneous or individual chamber measurement without having to physically move individual ATR substrates or chambers once alignment with the FTIR instrument is secured. Several IR-optical configurations can be used. FIGS. 11a-11c present different optical (i.e., IR source and detector) configurations for use with systems that include multiple ATR chambers and substrates. FIG. 11a shows an optical configuration of a basic design that couples multiple IR sources 50 and multiple IR detectors 52 to individual ATR substrates 26. Individual mirrors 54, e.g., single reflection mirrors, direct individual IR beams 40 from IR source 50 into respective ATR substrates 26 and subsequently direct IR light collected from the ATR substrates 26 to individual IR detectors 52 for measurement. FIG. 11b shows an optical configuration of a design that includes multiple IR sources 50 and a single IR defector 52, which are optically coupled to individual ATR substrates 26. Individual mirrors 54, e.g., single reflection mirrors, direct individual IR beams 40 from each IR source 50 into respective ATR substrates 26 and subsequently direct IR light collected from the individual ATR substrates 26 to a single detector 52, e.g., a multi-pixel array detector, for measurement. Detector array 52 is configured with pixels (not shown) that are positioned with a spacing that matches the ATR waveguides 26. This configuration eliminates defector variability, though pixels in the array can have different signal/noise ratios. The array detector configuration is also especially efficient when analyzing time-sensitive samples, as all of the ATR substrates can be analyzed in parallel, which eliminates artifacts introduced by different detectors. FIG. 11c shows an optical configuration of an integrated design that includes a single IR source 50 and a single IR detector 52, e.g., a multi-pixel array defector. A single IR light source 50 directs an IR beam 40 to each ATR waveguide 26 using a series of mirrors 54 coupled to a reciprocating mirror bank 56. This configuration eliminates variability inherent with use of individual and separate IR sources. Advantages of a single IR source and single IR detector design include: 1) fewer errors due to misalignment and IR losses; 2) reduced noise; 3) more compact; and is 4) an integrated system.

In an alternate configuration, multiple IR sources can be used with a single array detector. In this configuration, a reciprocating mirror bank can be used to direct light from the exit side of the ATR waveguides to the array detector instead of the entrance side. This configuration can be expected to substantially improve comparability between data collected from different ATR substrates, as the same detector would be used to process each dataset. This configuration may not be as efficient given that each ATR substrate is analyzed at a different time, possibly leading to longer windows of operation where other ATR substrates would not be analyzed. This configuration could be potentially detrimental to data collection for time-sensitive specimens. In yet another optical configuration, a single IR source can be coupled to a single multi-pixel array detector. In this configuration, a reciprocating mirror bank can be positioned to direct the IR source beam on the entrance side of the ATR waveguides. Straight reflecting mirrors can be positioned on the exit side of the ATR waveguides to direct the IR data-containing beam to the single array detector. This configuration can increase the signal to noise ratio attributed to using separate IR sources for each waveguide. The signal to noise ratio attributed to multiple detectors would be reduced by using an array detector. In still yet another optical configuration, a single IR source can be coupled to a single detector. In this configuration, two reciprocating mirror banks can be used. A first reciprocating mirror bank is positioned on the input side of the ATR waveguides. A second reciprocating mirror bank is positioned on the output side to direct light from the ATR waveguides to the array defector. This configuration is ideal for increasing signal to noise, as all ATR-waveguides would receive the same IR source beam, which would also be analyzed by the same detector. This configuration may not be as efficient as each ATR substrate is analyzed at a different time, giving potentially longer windows of operation, which is potentially detrimental to data collection for time-sensitive specimens. While a reciprocating mirror bank has been described, the invention is not limited thereto. Alternate methods of moving IR source light can also be used interchangeably, e.g., a movable IR source. A reciprocating mirror bank is preferable, as it is easily aligned. By incorporating multiple ATR substrates "chambers" in a multi-well system or device, it is possible to do a number of otherwise complex experiments including, e.g.; 1) determining the effect of different numbers of toxins on a single cell type growing in the same headspace environment. Here, one or more ATR substrates can be used as reference substrates for untreated samples; 2) using depth probing to determine what is happening at different layers inside a particular cell type. Identical ATR substrate types are used with different incidence angles ($\theta$), thereby effectively changing depth of penetration ($d_p$) values; and 3) determining effect of different ATR substrates on absorbance data. Several different ATR substrates can be used with different incidence angles ($\theta$), thereby yielding approximately the same average depth of penetration values. Such device configurations can achieve optimum signal to noise values from multiple experiments for rapid screening without introducing artifacts inherent in using multiple source/detection combinations with separate ATR waveguides. While preferred configurations are described, the invention is not limited. All instrument and device configurations selected by those of skill in the art in view of the disclosure are within the scope of the invention. No limitations are intended.

Advantages of the Invention

In order to monitor live-cells with infrared radiation, an ATR method must be used in order to prevent collecting background interference due to the atmospheric absorptions associated with the cellular nutrient media (i.e., water). In order to maximize the efficiency of the ATR method (i.e., minimize background absorptions due to media interactions), an ideal cell line to use for ATR experiments is one that can be grown to near 100% confluence, ATR devices known in the spectroscopic arts do not have the ability to achieve the needed confluence levels due to an inability to control the sample environment of the cells, a lack of a functionalized surface on which the cells can grow and attach, and various other features of the instant invention. Thus, the invention provides unique advantages over conventional ATR devices. The present invention provides the ability to consistently monitor IR signatures of cells growing on the ATR substrate in real time, and allows constant scans, one after the other, at frequencies where useful information can be gathered (e.g., near-IR, mid-IR, THz, mm-wave, Raman, etc.) and where total internal reflection can be utilized which depends on the type of ATR substrate used. The exemplary design allows cells to be analyzed at least once every ~30 minutes on average, although times are not limited thereto. A typical scan requires ~5-7 minutes, and cells cannot be out of the growth-supporting environment (enclosure vessel) for more than 10 minutes without showing signs of stress. Continuous monitoring provided by the present invention allows a researcher to define all IR-observable changes at time points near the actual dose (treatment) time virtually uninterrupted, as scans can be taken continuously. In addition, the design allows monitoring of cellular changes observable through IR absorption in vitro. Cells are grown on the ATR substrate directly and thus the same cells and regions of the same cells are always analyzed in each time event when data is collected. Conventional practices require a researcher to take aliquots from a Petri dish which means cells in the new aliquot may not be representative of cells examined in a previous sample. The present invention allows unhindered in situ FTIR absorption monitoring of live cells and prevents artifacts from being introduced as a consequence of moving the ATR substrate and medium from the incubator to the FTIR instrument for analysis, i.e., during data collection. Continuous shuttling of the FTIR-ATR chamber between the standard cell culture incubator and the FTIR system results in a number of artifacts being introduced into the measurement, including but not limited to the stress associated with maintaining the cells in a sub-optimal culture condition while in the FTIR equipment, spectral peak changes associated with the indicated stress, peak artifacts associated with changes in humidity levels within the FTIR chamber during such moves, and peak artifacts associated with small changes in the alignment of the ATR crystal within the chamber.

The invention provides accurate and real-time monitoring of changes in cellular responses to physical, chemical, and biological stimuli introduced to the cells in the enclosure. The invention provides the ability to monitor cellular response in vitro as the cell response can be correlated with the settling or arrival of the stimulus, e.g., a chemical or nanoparticles, near the surface of the cells. Cells can then be monitored in real time and their changes analyzed. Not only can the device monitor IR-observable cellular changes but it can also be used to monitor cell toxins that have an IR-observable chemical signature. For example, many toxins used to probe cells have a characteristic IR signature that can be monitored when added to the nutrient medium. Silica suspensions, e.g., have characteristic IR peaks and settling behavior that can be monitored using IR absorbance at characteristic frequencies. For example, settling of a micro-or nano-sized silica suspension (a toxin) can be monitored by observing increases in IR absorbance at their characteristic absorption frequencies (i.e., primary peak at ~1116 $cm^{-1}$), as described in reference to FIG. 6. Cell response can be correlated with the arrival of the toxin, or settling of the particle near the surface of the cells. This is a convenient advantage to using the ATR method for monitoring the cellular response in vitro. This is also critical in determining an exact dose of the toxin administered to the cells. The invention also removes many sources of error observed in conventional cell growth experiments. First, the invention removes alignment artifacts introduced into IR spectra in conventional spectroscopy from continuous coupling and decoupling of the ATR enclosure vessel as a researcher collects spectra. Each coupling/decoupling cycle with an ATR enclosure vessel can introduce small changes in signal intensity in the FTIR due to how the ATR enclosure vessel is seated, unless an alignment is performed after the ATR enclosure vessel is repositioned in the collection instrument prior to subsequent analysis. Later, as the researcher subtracts later spectra from initial spectra, signal changes introduced in the IR spectra in concert with how the ATR enclosure vessel was seated in the FTIR can appear as artifacts, artifacts which are not due to actual environmental or cellular changes. The invention can eliminate these artifacts because the ATR substrate can be aligned with the IR spectrometer once during each, live cell experiment, or can be re-aligned during/between data collection. Because drift and misalignment of the optics can occur in IR instruments over time, the invention also provides the ability to monitor the misalignment potential by collecting scans using a blank ATR plate, e.g., for up to 24 hours and monitoring the peak-to-peak centerburst to identify misalignment or drifting potential. Secondly, live cells are not physically disturbed, which prevents errors introduced as a consequence of physically disturbing/displacing cells and accidentally removing cells from the ATR substrate. Third, the state of live cells is maintained such that impacts of a particular stimulus (e.g., nanoparticles) on cells can be more accurately analyzed and assessed. For example, the state of cells on the ATR substrate is not altered due to exposing cells to less than ideal conditions that include, but are not limited to, e.g., low or high temperatures, low or high $CO_2$, low or high humidity, chemical equilibrium changes, physical changes, or combinations of these factors. The invention optimizes conditions that promote and sustain healthy cell growth. The invention further provides controls and regulation over: 1) environmental $CO_2$; 2) temperature; 3) humidity; and 4) aseptic growth environment. Further, the invention provides the ability to assess impacts of experimental conditions on live cells not provided by prior art devices. The invention provides a self-contained enclosure which provides a self-sustainable cellular growth environment that eliminates need for a separate vessel (e.g., an external incubator) to maintain cells for experiments. The invention monitors observable cellular changes at selected energies (e.g., near-IR, mid-IR, far-IR, THz, mm-wave, etc.) and can also be used to monitor responses to cell toxins. For example, when introduced or added to a cell medium, nanotoxins with an IR-observable chemical signature can be traced in vitro, as can the cellular responses to the toxins. For example, cell response can be correlated with the arrival of the toxin (e.g., as a particle) near the surface of the cells. Cell toxins include, but are not limited to, e.g., lipopolysaccharide (LPS), carbon nanotubes, and/or micro-silica and nano-silica suspensions. All chemical toxins that provide a suitable IR signature or suitable device response can be traced in conjunction with the present invention for a cell line being analyzed. The surface layer on the ATR provides an engineered boundary between the ATR sensing components and the biological organisms, thus enabling the two systems to function together. The surface layer provides the ability to use ATR systems and materials in aqueous systems. The surface layer provides the ability to grow high cell densities on the ATR surface with minimal perturbation to the cell function. The chemical nature of the surface layer can further be engineered to provide desired biochemical properties. Specific compositions are described subsequently but range from thicker protein coatings to high-density chemical monolayers. Without the surface chemistry layer, compatibility between the biological system and optical system can be limited, resulting in poor measurement performance.

INDUSTRIAL APPLICATIONS

Industrial applications for the invention include, but are not limited to, e.g., pharmaceutical drug screening; product testing (e.g., nanoparticles) for compliance with applicable regulations; biological monitoring of bacterial and algal cultures used in bio-pesticide production and aquaculture; studying chemistry and biochemistry of live cells; evaluating biomaterials (e.g., implants) and their interaction with live cells;

evaluating drug delivery systems and responses; studying biomolecules, biomolecule assemblies, and compatibility with live-cell systems; biological monitoring/sensing of live cells; and other cell responses and applications. The invention components can also be interfaced with any FTIR instrument and other potential analytical instruments, e.g., for chemical/biological characterization.

The following Examples provide a further understanding of the invention that provides for real-time, sustained analysis of live cells using ATR/FTIR,

EXAMPLE 1

Real-Time Monitoring of Cells Dosed with Silica Nanoparticles

Silica Settling

Mouse epithelial cells (e.g., C-10 epithelial cells, American Type Culture Collection, Manassas, Va., USA) were grown in a normal cell growth medium (e.g., CMRL-1066 medium, invitrogen, Carlsbad, Calif., USA) supplemented with 10% fetal bovine serum (FBS), 1% GlutaMAX-I™; 1% penicillin/streptomycin, all obtained commercially (invitrogen Corp., Carlsbad, Calif. USA). Cells were maintained at 37° C. and 5% $CO_2$ in a Water Jacketed $CO_2$ incubator with HEPA filter (e.g., a ThermoForma Series II Water Jacketed $CO_2$ incubator. Thermo Fisher Scientific, Inc., Waltham, Mass., USA). Cells were subcultured at 70-80% confluency from the incubator following standard protocols. Media was removed from the cells and Trypsin-EDTA (GIBCO, Grand Island, N.Y., USA) was added to detach cells from the cell culture plate. An equal volume of supplemented CMRL-1066 medium was added to the detached cells (as observed with a microscope) to stop the trypsinization process. Cells were then centrifuged at 1100×g for 5.0 min to form a cell pellet. Supernatant was aspirated, and the cell pellet was resuspended in 5 mL of supplemented CMRL-1066 growth media in preparation for transfer to the growth supporting environment (enclosure vessel) and attachment to the ATR substrate. The ATR substrate (ZnSe) was coated with a glycoprotein, e.g., FIBRONECTIN® (Sigma, St. Louis, Mo.) as follows, 10 μL of a 0.1 mg/mL FIBRONECTIN® stock solution was added to 100 μL of sterile deionized water (i.e., di-$H_2O$), which was spread over the surface of the ATR substrate using a sterile pipette tip. The ATR substrate was allowed to air dry in a sterile fume hood. 10 μL of 0.1 mg/mL FIBRONECTIN® stock solution was added to the C-10 cells (resuspended above) and the resuspended cells were transferred to the ATR enclosure vessel. Upon reaching 100% confluency, FTIR data were collected for the background. A sterile culture was maintained by doing all work in a sterile fume hood and fastening the lid to the ATR enclosure vessel prior to removal from the hood. The ATR enclosure vessel (and ATR substrate) was mounted to the FTIR for data collection. The ATR substrate was auto-aligned with the FTIR instrument (and mirrors) using Omnic 4.2a software (Thermo Electron, Madison, Wis. USA) to maximize the instrument signal-to-noise for a given defector gain setting without saturation of the detector. FTIR spectra were obtained at ~15 min intervals prior to the addition of nanoparticles and ~30 min intervals post treatment.

Nanoparticles to be added to 100% confluent cells were performed as follows. One drop (~50 ul) of a suspension containing 10 nm silica particles (e.g., Cat. No. 24298 silica microspheres, 0.01 μm broad distribution, 5 wt %, Polysciences, inc., Warrington, Pa., USA) was added to 150 μL of phosphate buffered saline (PBS) (e.g., Cat. No. 10010-023 potassium phosphate monobasic ($KH_2PO_4$) buffer, 144 mg/mL solution, invitrogen, Carlsbad, Calif., USA) in a microcentrifuge tube and vorfexed for 15 sec, and heated to 37° C. in a water bath (~10 min). ~15 min after collection of a pre-dose FTIR data point, buffered silica particle suspension (~200 μL) was evenly distributed across the top surface of the cell layer (culture media) atop the ATR substrate using a pipette. A zero time point was collected in the FTIR, with subsequent time points taken every ~30 min to observe spectral changes associated with settling of silica nanoparticles near the C-10 epithelial cells membrane surface. Data collection period was ~4.5 min per data point. Absorbance data were averaged and peak areas and peak heights analyzed using OMIC software. Results are presented in FIG. 6.

EXAMPLE 2

Real-Time Monitoring of Confluent Cells Treated with Tumor Promoter (bFGF)

Mouse cells (JB6 carcinogenesis mouse endothelial model cells) (clone 41-5a, ATCC, Manassas, Va., USA) were maintained in a minimal essential medium (MEM+GlutaMAX-I™, CISCO, Grand Island, N.Y.) supplemented with 5% fetal bovine serum (FBS) (Atlanta Biologicais, Norcross, Ga.) that further included: 1% penicillin/streptomycin (GIBCO, Grand Island, N.Y.) and an additional 1%. GlutaMAX-I™ (GIBCO, Grand Island, N.Y.). Cells were maintained at 37° C. and 5% $CO_2$ in an incubator (e.g., a ThermoForma Series II Water Jacketed $CO_2$ incubator. Thermo Fisher Scientific, inc., Waltham, Mass.) equipped with a HEPA filter. The JB6 cells were subcultured at 70-80% confluency following standard protocols. Media was removed from cells and Trypsin-EDTA (GIBCO, Grand island, N.Y.) was added to detach cells from the cell culture plate. An equal volume of the fluid medium that was supplemented with MEM+GlutaMAX-I™ was added to the detached cells (as observed with a microscope) to stop the trypsinization process. Cells were then centrifuged at 1100×g for 3.5 min to form a cell pellet. Supernatant was aspirated, and the cell pellet was resuspended in 5 ml of supplemented MEM+GlutaMAX-I™ media in preparation for transfer to the growth-supporting environment (enclosure vessel) and attachment to the ATR substrate. Prior to addition of cells to the growth-supporting environment, the ZnSe ATR substrate was coated with a glycoprotein, FIBRONECTIN® (Sigma, St. Louis, Mo.). 10 μl of a 0.1 mg/mL FIBRONECTIN® stock solution was added to 100 μL of sterile deionized water (i.e., di-$H_2O$). The solution was spread over the entire surface of the ATR substrate using a sterile pipette tip and allowed to air dry in a sterile fume hood. An additional 10 uL of 0.1 mg/mL FIBRONECTIN® was added to re-suspend the JB6 cell pellet and the total volume was transferred to the ATR enclosure vessel. A sterile culture was maintained by doing all work in a sterile fume hood and fastening the lid to the growth-supporting environment prior to removal from the hood and mounting on the FTIR. Gas (control) ports remained sealed in conjunction with quick connect connectors. Prior to commencing data collection, an input device (combination $CO_2$ controller device and humidifier device) (Simplex Scientific, Middleton, Wis., USA) was connected, which provided a $CO_2$ concentration of 5%, and the airspace above the media at a relative humidity of ~100%. A temperature of 37° C. in the enclosure vessel was maintained in conjunction with a heater. The ATR substrate was auto-aligned with the FTIR instrument using Omnic 4.2a software (Thermo Electron, Madison, Wis., USA), This routinely used automatic mirror alignment maximizes the instrument signal to noise for a given detector gain setting without saturation of the detector. Data was collected for 72 hours total at 15-minute intervals. Media was changed at 24 hours by moving the ATR enclosure vessel to a sterile hood. The system was perturbed by the addition of the tumor promoter bFGF at 48 hours. Data are presented in FIGS. 7a-7b.

We claim:

1. A device for monitoring IR-observable changes in live cells in real time, characterized by:
a growth-supporting environment that defines an enclosure vessel that includes an ATR substrate comprised of a preselected material and a functionalization layer that provides for attachment and growth of cells thereon, said growth-supporting environment is configured to grow and maintain cells of at least one biological organism to/at a preselected confluence atop said ATR substrate and to deliver an evanescent IR beam through said ATR substrate that monitors IR-observable changes in said cells in real-time.

2. The device of claim 1, wherein said ATR substrate is selected from the group consisting of: ZnSe, ZnS, Si, Ge, AMTIR, and combinations thereof.

3. The device of claim 2, wherein said ATR substrate includes an incidence angle of from 30° to 80°.

4. The device of claim 3, wherein said ATR substrate is ZnSe that includes a 45° incidence angle.

5. The device of claim 1, further includes a trough that surrounds said ATR substrate, said trough includes at least one side positioned at a preselected angle that maintains contact between cells attached to said ATR substrate and a nutrient medium or fluid introduced to said growth-supporting environment.

6. The device of claim 5, wherein said trough includes at least one side with a preselected angle in the range from about 40° to 90°.

7. The device of claim 1, further includes at least one port for introduction or removal of a fluid.

8. The device of claim 7, wherein said fluid is an environmental gas.

9. The device of claim 1, further includes a heater that provides temperature control within said growth-supporting environment.

10. The device of claim 1, further includes at least one sensor that monitors concentration of at least one gas within said supporting environment.

11. The device of claim 1, further includes a humidifier that provides a preselected humidity within said growth-supporting environment.

12. The device of claim 1, further includes a lid with a viewport for viewing and imaging of internal contents within said growth-supporting environment.

13. The device of claim 1, further includes a carousel stage with at least o ATR substrates mounted thereto.

14. A system for monitoring live-cells in a biological monitoring process in real-time, comprising:
a growth-supporting environment that defines an enclosure;
an ATR substrate located within said growth-supporting environment that includes live cells at a preselected confluence positioned on a surface of said ATR substrate; and
a trough that surrounds said ATR substrate, said trough includes at least one side oriented at a preselected angle;
said growth-supporting environment detachably couples to, and operably aligns with, an infrared instrument and delivers an evanescent IR beam through said ATR substrate for monitoring IR-observable changes in said cells in real-time.

15. The system of claim 14, wherein said ATR substrate further includes a functionalization layer that provides for attachment and growth of said cells on said surface of said ATR substrate within said growth-supporting environment.

16. The system of claim 15, wherein said functionalization layer comprises a structured fiber.

17. The system of claim 16, wherein said structured fiber is an AMTIR fiber.

18. The system of claim 15, wherein said functionalization layer includes a cell growth reagent.

19. The system of claim 18, wherein said cell growth reagent includes a glycoprotein.

20. The system of claim 15, wherein said functionalization layer has a thickness greater than or equal to about 0.5 nm.

21. The system of claim 15, wherein said functionalization layer has a thickness selected in the range from about 3 nm to about 10 nm.

22. The system of claim 14, wherein said preselected confluence of said cells is greater than about 40%.

23. The system of Claire 14, wherein said growth-supporting environment includes a cell nutrient medium in fluid contact with said cells on said surface of said ATR substrate that maintains vitality of said live cells therein.

24. The system of claim 23, wherein said trough maintains contact between said nutrient medium and said cells on said surface of said ATR substrate.

25. The system of claim 14, further includes at least one port for introduction or removal of a preselected physiologic gas, fluid, or constituent.

26. The system of claim 14, further includes at least one optically transparent viewport for monitoring of cells introduced to said surface of said ATR substrate.)

27. The system of claim 14, further includes at least one sensor.

28. The system of claim 14, further includes a temperature control device.

29. The system of claim 14, further includes a humidity control device.

30. The system of claim 14, wherein said growth-supporting environment when coupled to said infrared instrument provides continuous real-time data of said live cells over a preselected time interval.

31. The system of claim 30, wherein said preselected time interval is a time greater than or equal to about 2 hours.

32. The system of claim 14, further includes a carousel stage that includes a plurality of ATR substrates mounted thereto, said carousel is rotable clockwise or counterclockwise to allow loading, selection, and/or analysis of at least one sample introduced thereto.

33. The system of claim 14, wherein said ATR substrate includes an edge with an angle selected in the range from about 30° to about 60°.

34. The system of claim 14, wherein said growth-supporting environment includes at least two ATR substrates.

35. The system of claim 14, wherein said IR instrument includes:
an IR radiation source operatively coupled to said ATR substrate that transmits an evanescent IR wave through said ATR substrate in at least one optical mode; and
a detector for detecting said evanescent IR wave that transmits through said ATR substrate;
said system provides monitoring of said live cells in contact with said ATR substrate in real-time.

36. A device for monitoring IR-observable changes in live cells in real time, characterized by:
  a growth-supporting environment that defines an enclosure vessel with at least one port for introduction or removal of a fluid, said growth-supporting environment includes an ATR substrate comprised of a preselected material configured to grow and maintain cells of at least one biological organism to/at a preselected confluence atop said ATR substrate and to deliver an evanescent IR beam through said ATR substrate that monitors IR-observable changes in said cells in real-time.

37. The device of claim 36, wherein said ATR substrate is selected from the group consisting of: ZnSe, ZnS, Si, Ge, AMTIR, and combinations thereof.

38. The device of claim 37, wherein said ATR substrate includes an incidence angle of from 30° to 80°.

39. The device of claim 36, wherein said ATR substrate includes a functionalization layer that provides for attachment and growth of said cells within said growth-supporting environment.

40. The device of claim 36, further includes a trough that surrounds said ATR substrate with at least one side positioned at a preselected angle that maintains contact between cells attached to said ATR substrate and a nutrient medium or fluid introduced to said growth-supporting environment.

41. The device of claim 36, wherein said fluid is an environmental gas.

42. A device for monitoring IR-observable changes in live cells in real time, characterized by:
  a growth-supporting environment that defines an enclosure vessel that includes a carousel stage with at least two ATR substrates comprised of a preselected material mounted thereto, said growth-supporting environment is configured to grow and maintain cells of at least one biological organism to/at a preselected confluence atop said ATR substrates and to deliver an evanescent IR beam through said ATR substrates that monitors IR-observable changes in said cells in real-time.

43. The device of claim 42, wherein said ATR substrate is selected from the group consisting of: ZnSe, ZnS, Si, Ge, AMTIR, and combinations thereof.

44. The device of claim 43, wherein said ATR substrate includes an incidence angle of from 30° to 80°.

45. The device of claim 44, wherein said ATR substrate is ZnSe that includes a 45° incidence angle.

46. The device of claim 42, wherein said ATR substrate includes a functionalization layer that provides for attachment and growth of said cells within said growth-supporting environment.

47. The device of claim 42, further includes a trough that surrounds said ATR substrate, said trough includes at least one side positioned at a preselected angle that maintains contact between cells attached to said ATR substrate and a nutrient medium or fluid introduced to said growth-supporting environment.

48. The device of claim 42, further includes at least one port for introduction or removal of a fluid.

49. The device of claim 48, wherein said fluid is an environmental gas.

50. The device of claim 42, further includes a heater that provides temperature control within said growth-supporting environment.

51. The device of claim 42, further includes at least one sensor that monitors concentration of at least one gas within said supporting environment.

52. The device of claim 42, further includes a humidifier that provides a preselected humidity within said growth-supporting environment.

53. The device of claim 42, further includes a lid with a viewport for viewing and imaging of internal contents within said growth-supporting environment.

54. A device for monitoring IR-observable changes in live cells in real time, characterized by:
  a growth-supporting environment that defines an enclosure vessel that includes an ATR substrate comprised of a preselected material, said growth-supporting environment is configured to grow and maintain cells of at least one biological organism tolat a preselected confluence atop said ATR substrate and to deliver an evanescent IR beam through said ATR substrate that monitors IR-observable changes in said cells in real-time, and a lid with a viewport for viewing and imaging of internal contents within said growth-supporting environment.

55. A device for monitoring IR-observable changes in live cells in real time, characterized by:
  a growth-supporting environment that defines an enclosure vessel that includes an ATR substrate comprised of a preselected material configured to grow and maintain cells of at least one biological organism to/at a preselected confluence atop said ATR substrate and to deliver an evanescent IR beam through said ATR substrate that monitors IR-observable changes in said cells in real-time, and a humidifier that provides a preselected humidity within said growth -supporting environment.

56. A device for monitoring IR-observable changes in live cells in real time, characterized by:
  a growth-supporting environment that defines an enclosure vessel that includes an ATR substrate comprised of a preselected material that is configured to grow and maintain cells of at least one biological organism to/at a preselected confluence atop said ATR substrate and to deliver an evanescent IR beam through said ATR substrate that monitors IR-observable changes in said cells in real-time, and at least one sensor that monitors concentration of at least one gas within said growth-supporting environment.

57. A device for monitoring IR-observable changes in live cells in real time, characterized by:
  a growth-supporting environment that defines an enclosure vessel that includes an ATR substrate comprised of a preselected material that is configured to grow and maintain cells of at least one biological organism to/at a preselected confluence atop said ATR substrate and to deliver an evanescent IR beam through said ATR substrate that monitors IR-observable changes in said cells in real-time, and a heater that provides temperature control within said growth-supporting environment.

* * * * *

UNITED STATES PATENT AND TRADEMARK OFFICE
CERTIFICATE OF CORRECTION

PATENT NO. : 7,956,328 B2
APPLICATION NO. : 12/511833
DATED : June 7, 2011
INVENTOR(S) : S. Kamakshi Sundaram et al.

It is certified that error appears in the above-identified patent and that said Letters Patent is hereby corrected as shown below:

Col. 1, line 16: replace "five" with "live"

Col. 1, line 41: replace ""nanomatehals" with "nanomaterials"

Col. 1, line 42: replace "In" with "in"

Col. 3, line 7: replace "humidify" with "humidity"

Col. 3, line 29: replace "ox" with "or"

Col. 3, line 63: replace "humidify" with "humidity"

Col. 4, line 26: replace "humidify" with "humidity"

Col. 4, line 40: replace "feast" with "least"

Col. 5, line 7: replace "defector" with "detector"

Col. 6, line 38: replace "nanofoxin" with "nanotoxin"

Col. 7, line 34: replace "nanofoxin" with "nanotoxin"

Col. 8, line 52: replace "HERA" with "HEPA"

Col. 9, line 24: replace "five" with "live"

Col. 10, line 26: replace "28" with "26"

Col. 10, line 49: replace "infernal" with "internal"

Col. 11, line 6: replace "intensify" with "intensity"

Col. 12, line 59: replace "$\lambda$" with "$\theta$"

Col. 14, line 24: replace "30" with "36"

Col. 14, line 28: replace "infernally" with "internally"

Col. 14, line 61: replace "28" with "26"

Col. 14, line 61: replace "info" with "into"

Col. 14, line 64, replace "info" with "into"

Col 15, line 24: replace "MB" with "ATR"

Signed and Sealed this
Twenty-fifth Day of October, 2011

David J. Kappos
*Director of the United States Patent and Trademark Office*

CERTIFICATE OF CORRECTION (continued)
U.S. Pat. No. 7,956,328 B2

Col. 16, line 50: replace "stereoscopically" with "spectroscopically"

Col. 17, line 24: replace "intensify" with "intensity"

Col. 17, line 53: replace "20" with "26"

Col. 17, line 58: replace "info" with "into"

Col. 18, line 5: replace "28" with "26"

Col. 18, line 33: replace "defector" with "detector"

Col. 19, line 28: replace "defector" with "detector"

Col. 19, line 35: replace "defector" with "detector"

Col. 20, line 6: replace "defector" with "detector"

Col. 21, line 11: replace "fake" with "take"

Col. 21, line 34: replace "nanoparticles" with "nanoparticle"

Col. 24, line 26: replace "Biologicais" with "Biologicals"

Col. 25, line 55: replace "o" with "two"

Col. 26, line 24: replace "Claire" with "Claim"

Col. 28, line 19: replace "tolat" with "to/at"